United States Patent
Wong et al.

(10) Patent No.: US 6,331,614 B1
(45) Date of Patent: Dec. 18, 2001

(54) HUMAN CDC14A GENE

(75) Inventors: Alexander K. C. Wong, La Jolla, CA (US); David H. -F. Teng; Sean V. Tavtigian, both of Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/468,872

(22) Filed: Dec. 22, 1999

Related U.S. Application Data

(60) Provisional application No. 60/113,833, filed on Dec. 23, 1998.

(51) Int. Cl.$^7$ .......................... C07H 21/04; C07H 21/02; C12N 15/00; C12N 15/09; C12N 15/63
(52) U.S. Cl. .................. 536/23.5; 536/23.1; 435/320.1; 435/325
(58) Field of Search .................. 536/23.1, 23.5; 435/320.1, 325

(56) References Cited

PUBLICATIONS

GenBank Accession No. AF064102, L. Hao et al., Aug. 1999, 1153.*
Li et al, 1997, J. Biol. Chem., 272(47): 29403–29406.*
Wong et al, 1999, Genomics, 59(2): 248–251.*

* cited by examiner

*Primary Examiner*—Robert A. Schwartzman
*Assistant Examiner*—Peter Paras, Jr.
(74) *Attorney, Agent, or Firm*—Rothwell, Figg, Ernst & Manbeck

(57) ABSTRACT

The present invention relates generally to the field of human genetics. Specifically, the present invention relates to human CDC14A gene which has been found to be mutated in certain tumor cell lines. More specifically, the invention relates to a novel sequence for the human CDC14A gene. The present invention further relates to somatic mutations in the CDC14A gene in human cancer and their use in the diagnosis and prognosis of human cancer. The invention also relates to the therapy of human cancers which have a mutation in the CDC14A gene, including gene therapy, protein replacement therapy and protein mimetics. The invention further relates to the screening of drugs for cancer therapy. Finally, the invention relates to the screening of the CDC14A gene for mutations, which are useful for diagnosing the predisposition to cancer.

14 Claims, 1 Drawing Sheet

SEQUENCE LISTING

<160> NUMBER OF SEQ ID NOS: 82

<210> SEQ ID NO 1
<211> LENGTH: 1785
<212> TYPE: DNA
<213> ORGANISM: Homo sapiens
<220> FEATURE:
<221> NAME/KEY: CDS
<222> LOCATION: (1)..(1782)

<400> SEQUENCE: 1

```
atg gca gcg gag tca ggg gaa cta atc ggg gct tgt gag ttc atg aaa      48
Met Ala Ala Glu Ser Gly Glu Leu Ile Gly Ala Cys Glu Phe Met Lys
  1               5                  10                  15 gat cgg tta tat ttt gct act tta agg aat aga cca aaa agc aca gta      96
Asp Arg Leu Tyr Phe Ala Thr Leu Arg Asn Arg Pro Lys Ser Thr Val
             20                  25                  30 aat acc cac tat ttc tcc atc gat gag gag ctg gtc tat gaa aat ttc     144
Asn Thr His Tyr Phe Ser Ile Asp Glu Glu Leu Val Tyr Glu Asn Phe
         35                  40                  45 tat gca gat ttt gga ccg ctg aac ttg gca atg gtg tac aga tat tgc     192
Tyr Ala Asp Phe Gly Pro Leu Asn Leu Ala Met Val Tyr Arg Tyr Cys
     50                  55                  60 tgc aaa cta aac aag aaa cta aaa tca tac agt ttg tca aga aag aaa     240
Cys Lys Leu Asn Lys Lys Leu Lys Ser Tyr Ser Leu Ser Arg Lys Lys
 65                  70                  75                  80 ata gtg cac tac acc tgt ttt gac caa cgg aaa aga gca aat gca gca     288
Ile Val His Tyr Thr Cys Phe Asp Gln Arg Lys Arg Ala Asn Ala Ala
                 85                  90                  95
```

-continued

```
ttt ttg ata ggt gcc tat gca gta atc tat tta aag aag aca cca gaa      336
Phe Leu Ile Gly Ala Tyr Ala Val Ile Tyr Leu Lys Lys Thr Pro Glu
            100                 105                 110 gaa gcc tac aga gca ctc ctg tct ggc tca aac ccc ccc tat ctt cca      384
Glu Ala Tyr Arg Ala Leu Leu Ser Gly Ser Asn Pro Pro Tyr Leu Pro
        115                 120                 125 ttc agg gat gct tcc ttt gga aat tgc act tac aat ctc acc att ctc      432
Phe Arg Asp Ala Ser Phe Gly Asn Cys Thr Tyr Asn Leu Thr Ile Leu
    130                 135                 140 gac tgt ttg cag gga atc aga aag gga tta caa cat gga ttt ttt gac      480
Asp Cys Leu Gln Gly Ile Arg Lys Gly Leu Gln His Gly Phe Phe Asp
145                 150                 155                 160 ttt gag aca ttt gat gtg gat gaa tat gaa cat tat gag cga gtt gaa      528
Phe Glu Thr Phe Asp Val Asp Glu Tyr Glu His Tyr Glu Arg Val Glu
                165                 170                 175 aat ggt gac ttc aac tgg att gtt cca gga aaa ttt tta gca ttt agt      576
Asn Gly Asp Phe Asn Trp Ile Val Pro Gly Lys Phe Leu Ala Phe Ser
            180                 185                 190 gga cca cat cct aaa agc aaa att gag aat ggt tat cct ctt cac gcc      624
Gly Pro His Pro Lys Ser Lys Ile Glu Asn Gly Tyr Pro Leu His Ala
        195                 200                 205 cct gaa gcc tac ttt cct tat ttc aaa aag cat aat gtg act gca gtt      672
Pro Glu Ala Tyr Phe Pro Tyr Phe Lys Lys His Asn Val Thr Ala Val
    210                 215                 220 gtg agg cta aac aaa aag att tat gag gca aag cgc ttc aca gac gct      720
Val Arg Leu Asn Lys Lys Ile Tyr Glu Ala Lys Arg Phe Thr Asp Ala
225                 230                 235                 240 ggc ttc gag cac tat gac ctc ttc ttc ata gat ggc agc aca ccc agt      768
Gly Phe Glu His Tyr Asp Leu Phe Phe Ile Asp Gly Ser Thr Pro Ser
                245                 250                 255 gac aac atc gtg cga agg ttc ctg aac atc tgt gag aac acc gaa ggg      816
Asp Asn Ile Val Arg Arg Phe Leu Asn Ile Cys Glu Asn Thr Glu Gly
            260                 265                 270 gcc atc gcc gtt cac tgc aaa gct ggt ctt gga aga aca ggg aca ttg      864
Ala Ile Ala Val His Cys Lys Ala Gly Leu Gly Arg Thr Gly Thr Leu
        275                 280                 285 ata gcc tgt tat gta atg aaa cac tac agg ttt aca cat gct gaa ata      912
Ile Ala Cys Tyr Val Met Lys His Tyr Arg Phe Thr His Ala Glu Ile
    290                 295                 300 att gct tgg att aga ata tgc cgg cca ggc tct att ata gga ccc cag      960
Ile Ala Trp Ile Arg Ile Cys Arg Pro Gly Ser Ile Ile Gly Pro Gln
305                 310                 315                 320 cag cac ttc ctg gaa gaa aaa caa gca tcg ttg tgg tca caa gga gac     1008
Gln His Phe Leu Glu Glu Lys Gln Ala Ser Leu Trp Val Gln Gly Asp
                325                 330                 335 att ttc cga tcc aaa ctg aaa aat cga cca tcc agt gaa gga agt att     1056
Ile Phe Arg Ser Lys Leu Lys Asn Arg Pro Ser Ser Glu Gly Ser Ile
            340                 345                 350 aat aaa att ctt tct ggc cta gat gat atg tct att ggt gga aat ctt     1104
Asn Lys Ile Leu Ser Gly Leu Asp Asp Met Ser Ile Gly Gly Asn Leu
        355                 360                 365 tca aaa aca caa aac atg gaa cga ttt gga gag gat aac tta gaa gat     1152
Ser Lys Thr Gln Asn Met Glu Arg Phe Gly Glu Asp Asn Leu Glu Asp
    370                 375                 380 gat gat gtg gaa atg aaa aat ggt ata acc cag gga gac aaa cta cgt     1200
Asp Asp Val Glu Met Lys Asn Gly Ile Thr Gln Gly Asp Lys Leu Arg
385                 390                 395                 400 gcc tta aaa agt cag aga cag cca cgt acc tca cca tcc tgt gca ttt     1248
Ala Leu Lys Ser Gln Arg Gln Pro Arg Thr Ser Pro Ser Cys Ala Phe
```

-continued

```
            405                 410                 415
agg tca gat gat aca aaa gga cat cca aga gca gtg tcc cag cct ttc    1296
Arg Ser Asp Asp Thr Lys Gly His Pro Arg Ala Val Ser Gln Pro Phe
            420                 425                 430 aga tta agt tca tcc ctg caa gga tct gca gtt act ttg aag aca tca    1344
Arg Leu Ser Ser Ser Leu Gln Gly Ser Ala Val Thr Leu Lys Thr Ser
            435                 440                 445 aaa atg gca ctg tcc cct tca gca acg gcc aag agg atc aac aga act    1392
Lys Met Ala Leu Ser Pro Ser Ala Thr Ala Lys Arg Ile Asn Arg Thr
            450                 455                 460 tct ttg tct tcg ggt gcc act gta aga agc ttt tcc ata aac tcc cgg    1440
Ser Leu Ser Ser Gly Ala Thr Val Arg Ser Phe Ser Ile Asn Ser Arg
465                 470                 475                 480 cta gcc agt tct cta ggg aac ttg aat gct gca aca gat gat cca gag    1488
Leu Ala Ser Ser Leu Gly Asn Leu Asn Ala Ala Thr Asp Asp Pro Glu
                485                 490                 495 aac aaa aag acc tcc tca tcc tct aag gca ggc ttc aca gcc agc ccg    1536
Asn Lys Lys Thr Ser Ser Ser Ser Lys Ala Gly Phe Thr Ala Ser Pro
            500                 505                 510 ttt acc aac ctc ttg aat ggc agc tcc cag cca act acc aga aat tac    1584
Phe Thr Asn Leu Leu Asn Gly Ser Ser Gln Pro Thr Thr Arg Asn Tyr
            515                 520                 525 cct gag ctc aac aat aat cag tac aac aga agc agc aac agc aac ggg    1632
Pro Glu Leu Asn Asn Asn Gln Tyr Asn Arg Ser Ser Asn Ser Asn Gly
530                 535                 540 ggc aac ctg aac agc ccc cca ggc ccc cac agc gcc aag aca gag gag    1680
Gly Asn Leu Asn Ser Pro Pro Gly Pro His Ser Ala Lys Thr Glu Glu
545                 550                 555                 560 cac acc acc atc ctc cga ccc tcc tac acc ggg ctt tct tct tct tca    1728
His Thr Thr Ile Leu Arg Pro Ser Tyr Thr Gly Leu Ser Ser Ser Ser
                565                 570                 575 gcg aga ttc ctg agc cgt tct atc cct tcc ctt cag tct gaa tat gtt    1776
Ala Arg Phe Leu Ser Arg Ser Ile Pro Ser Leu Gln Ser Glu Tyr Val
            580                 585                 590 cat tac taa                                                        1785
His Tyr
```

<210> SEQ ID NO 2
<211> LENGTH: 594
<212> TYPE: PRT
<213> ORGANISM: Homo sapiens

<400> SEQUENCE: 2

```
Met Ala Ala Glu Ser Gly Glu Leu Ile Gly Ala Cys Glu Phe Met Lys
  1               5                  10                  15

Asp Arg Leu Tyr Phe Ala Thr Leu Arg Asn Arg Pro Lys Ser Thr Val
                 20                  25                  30

Asn Thr His Tyr Phe Ser Ile Asp Glu Glu Leu Val Tyr Glu Asn Phe
             35                  40                  45

Tyr Ala Asp Phe Gly Pro Leu Asn Leu Ala Met Val Tyr Arg Tyr Cys
         50                  55                  60

Cys Lys Leu Asn Lys Lys Leu Lys Ser Tyr Ser Leu Ser Arg Lys Lys
 65                  70                  75                  80

Ile Val His Tyr Thr Cys Phe Asp Gln Arg Lys Arg Ala Asn Ala Ala
                 85                  90                  95

Phe Leu Ile Gly Ala Tyr Ala Val Ile Tyr Leu Lys Lys Thr Pro Glu
            100                 105                 110

Glu Ala Tyr Arg Ala Leu Leu Ser Gly Ser Asn Pro Pro Tyr Leu Pro
```

```
                   115                 120                 125
Phe Arg Asp Ala Ser Phe Gly Asn Cys Thr Tyr Asn Leu Thr Ile Leu
    130                 135                 140

Asp Cys Leu Gln Gly Ile Arg Lys Gly Leu Gln His Gly Phe Phe Asp
145                 150                 155                 160

Phe Glu Thr Phe Asp Val Asp Glu Tyr Glu His Tyr Glu Arg Val Glu
                165                 170                 175

Asn Gly Asp Phe Asn Trp Ile Val Pro Gly Lys Phe Leu Ala Phe Ser
            180                 185                 190

Gly Pro His Pro Lys Ser Lys Ile Glu Asn Gly Tyr Pro Leu His Ala
        195                 200                 205

Pro Glu Ala Tyr Phe Pro Tyr Phe Lys Lys His Asn Val Thr Ala Val
    210                 215                 220

Val Arg Leu Asn Lys Lys Ile Tyr Glu Ala Lys Arg Phe Thr Asp Ala
225                 230                 235                 240

Gly Phe Glu His Tyr Asp Leu Phe Phe Ile Asp Gly Ser Thr Pro Ser
                245                 250                 255

Asp Asn Ile Val Arg Arg Phe Leu Asn Ile Cys Glu Asn Thr Glu Gly
            260                 265                 270

Ala Ile Ala Val His Cys Lys Ala Gly Leu Gly Arg Thr Gly Thr Leu
        275                 280                 285

Ile Ala Cys Tyr Val Met Lys His Tyr Arg Phe Thr His Ala Glu Ile
    290                 295                 300

Ile Ala Trp Ile Arg Ile Cys Arg Pro Gly Ser Ile Ile Gly Pro Gln
305                 310                 315                 320

Gln His Phe Leu Glu Glu Lys Gln Ala Ser Leu Trp Val Gln Gly Asp
                325                 330                 335

Ile Phe Arg Ser Lys Leu Lys Asn Arg Pro Ser Ser Glu Gly Ser Ile
            340                 345                 350

Asn Lys Ile Leu Ser Gly Leu Asp Asp Met Ser Ile Gly Gly Asn Leu
        355                 360                 365

Ser Lys Thr Gln Asn Met Glu Arg Phe Gly Glu Asp Asn Leu Glu Asp
    370                 375                 380

Asp Asp Val Glu Met Lys Asn Gly Ile Thr Gln Gly Asp Lys Leu Arg
385                 390                 395                 400

Ala Leu Lys Ser Gln Arg Gln Pro Arg Thr Ser Pro Ser Cys Ala Phe
                405                 410                 415

Arg Ser Asp Asp Thr Lys Gly His Pro Arg Ala Val Ser Gln Pro Phe
            420                 425                 430

Arg Leu Ser Ser Leu Gln Gly Ser Ala Val Thr Leu Lys Thr Ser
        435                 440                 445

Lys Met Ala Leu Ser Pro Ser Ala Thr Ala Lys Arg Ile Asn Arg Thr
    450                 455                 460

Ser Leu Ser Ser Gly Ala Thr Val Arg Ser Phe Ser Ile Asn Ser Arg
465                 470                 475                 480

Leu Ala Ser Ser Leu Gly Asn Leu Asn Ala Ala Thr Asp Asp Pro Glu
                485                 490                 495

Asn Lys Lys Thr Ser Ser Ser Lys Ala Gly Phe Thr Ala Ser Pro
            500                 505                 510

Phe Thr Asn Leu Leu Asn Gly Ser Ser Gln Pro Thr Thr Arg Asn Tyr
        515                 520                 525

Pro Glu Leu Asn Asn Asn Gln Tyr Asn Arg Ser Ser Asn Ser Asn Gly
    530                 535                 540
```

```
Gly Asn Leu Asn Ser Pro Pro Gly Pro His Ser Ala Lys Thr Glu Glu
545                 550                 555                 560

His Thr Thr Ile Leu Arg Pro Ser Tyr Thr Gly Leu Ser Ser Ser Ser
                565                 570                 575

Ala Arg Phe Leu Ser Arg Ser Ile Pro Ser Leu Gln Ser Glu Tyr Val
            580                 585                 590

His Tyr

<210> SEQ ID NO 3
<211> LENGTH: 21
<212> TYPE: DNA
<213> ORGANISM: Homo sapiens

<400> SEQUENCE: 3
ctccctcggc caggcttgtt g                                               21

<210> SEQ ID NO 4
<211> LENGTH: 25
<212> TYPE: DNA
<213> ORGANISM: Homo sapiens

<400> SEQUENCE: 4
ttgaaagatt tccaccaata gacat                                           25

<210> SEQ ID NO 5
<211> LENGTH: 38
<212> TYPE: DNA
<213> ORGANISM: Homo sapiens

<400> SEQUENCE: 5
gttttcccag tcacgacgtg acctcagctg gccacgac                             38

<210> SEQ ID NO 6
<211> LENGTH: 40
<212> TYPE: DNA
<213> ORGANISM: Homo sapiens

<400> SEQUENCE: 6
aggaaacagc tatgaccatt tccgttggtc aaaacaggtg                           40

<210> SEQ ID NO 7
<211> LENGTH: 41
<212> TYPE: DNA
<213> ORGANISM: Homo sapiens

<400> SEQUENCE: 7
gttttcccag tcacgacgga tattgctgca aactaaacaa g                         41

<210> SEQ ID NO 8
<211> LENGTH: 42
<212> TYPE: DNA
<213> ORGANISM: Homo sapiens

<400> SEQUENCE: 8
aggaaacagc tatgaccatc cacatcaatt gtctcaaagt ca                        42

<210> SEQ ID NO 9
<211> LENGTH: 41
<212> TYPE: DNA
<213> ORGANISM: Homo sapiens

<400> SEQUENCE: 9
```

-continued gttttcccag tcacgacgat ctcaccattc tcgactgttt g        41

<210> SEQ ID NO 10
<211> LENGTH: 40
<212> TYPE: DNA
<213> ORGANISM: Homo sapiens

<400> SEQUENCE: 10
aggaaacagc tatgaccatt gctcgaagcc agcgtctgtg          40

<210> SEQ ID NO 11
<211> LENGTH: 42
<212> TYPE: DNA
<213> ORGANISM: Homo sapiens

<400> SEQUENCE: 11
gttttcccag tcacgacgta tttcaaaaag cataatgtga ct       42

<210> SEQ ID NO 12
<211> LENGTH: 40
<212> TYPE: DNA
<213> ORGANISM: Homo sapiens

<400> SEQUENCE: 12
aggaaacagc tatgaccatg gggtcctata atagagcctg          40

<210> SEQ ID NO 13
<211> LENGTH: 22
<212> TYPE: DNA
<213> ORGANISM: Homo sapiens

<400> SEQUENCE: 13
catctgtgag aacaccgaag gg                             22

<210> SEQ ID NO 14
<211> LENGTH: 24
<212> TYPE: DNA
<213> ORGANISM: Homo sapiens

<400> SEQUENCE: 14
gcatttatag tagtcattaa ccag                           24

<210> SEQ ID NO 15
<211> LENGTH: 41
<212> TYPE: DNA
<213> ORGANISM: Homo sapiens

<400> SEQUENCE: 15
gttttcccag tcacgacgta tgtaatgaaa cactacaggt t        41

<210> SEQ ID NO 16
<211> LENGTH: 42
<212> TYPE: DNA
<213> ORGANISM: Homo sapiens

<400> SEQUENCE: 16
aggaaacagc tatgaccatt tttcatttcc acatcatcat ct       42

<210> SEQ ID NO 17
<211> LENGTH: 41
<212> TYPE: DNA
<213> ORGANISM: Homo sapiens -continued

```
<210> SEQ ID NO 18
<211> LENGTH: 40
<212> TYPE: DNA
<213> ORGANISM: Homo sapiens

<400> SEQUENCE: 18
aggaaacagc tatgaccatt tgctgaaggg gacagtgcca                    40

<210> SEQ ID NO 19
<211> LENGTH: 40
<212> TYPE: DNA
<213> ORGANISM: Homo sapiens

<400> SEQUENCE: 19
gttttcccag tcacgacggc ctttcagatt aagttcatcc                    40

<210> SEQ ID NO 20
<211> LENGTH: 41
<212> TYPE: DNA
<213> ORGANISM: Homo sapiens

<400> SEQUENCE: 20
aggaaacagc tatgaccatg ctcagggtaa tttctggtag t                  41

<210> SEQ ID NO 21
<211> LENGTH: 39
<212> TYPE: DNA
<213> ORGANISM: Homo sapiens

<400> SEQUENCE: 21
gttttcccag tcacgacgct tcacagccag cccgtttac                     39

<210> SEQ ID NO 22
<211> LENGTH: 40
<212> TYPE: DNA
<213> ORGANISM: Homo sapiens

<400> SEQUENCE: 22
aggaaacagc tatgaccatc tctccactgc tcgtccagat                    40

<210> SEQ ID NO 23
<211> LENGTH: 20
<212> TYPE: DNA
<213> ORGANISM: Homo sapiens

<400> SEQUENCE: 23
cgctgacccc gaagccgcct                                          20

<210> SEQ ID NO 24
<211> LENGTH: 21
<212> TYPE: DNA
<213> ORGANISM: Homo sapiens

<400> SEQUENCE: 24
cgattagttc cctgactccg c                                        21

<210> SEQ ID NO 25
<211> LENGTH: 24
<212> TYPE: DNA
<213> ORGANISM: Homo sapiens
```

<400> SEQUENCE: 17
gttttcccag tcacgacgat atgtctattg gtggaaatct t                  41

```
<400> SEQUENCE: 25
tttgggaagt cagtttagtt acac                                              24

<210> SEQ ID NO 26
<211> LENGTH: 24
<212> TYPE: DNA
<213> ORGANISM: Homo sapiens

<400> SEQUENCE: 26
cagaagaaat attcagtgaa ttct                                              24

<210> SEQ ID NO 27
<211> LENGTH: 23
<212> TYPE: DNA
<213> ORGANISM: Homo sapiens

<400> SEQUENCE: 27
taagttcatc cctgcaagga tct                                               23

<210> SEQ ID NO 28
<211> LENGTH: 23
<212> TYPE: DNA
<213> ORGANISM: Homo sapiens

<400> SEQUENCE: 28
acaaagaagt tctgttgatc ctc                                               23

<210> SEQ ID NO 29
<211> LENGTH: 22
<212> TYPE: DNA
<213> ORGANISM: Homo sapiens

<400> SEQUENCE: 29
gccagacaag aggcacagat tc                                                22

<210> SEQ ID NO 30
<211> LENGTH: 22
<212> TYPE: DNA
<213> ORGANISM: Homo sapiens

<400> SEQUENCE: 30
agtcaccttt caaatactgc gg                                                22

<210> SEQ ID NO 31
<211> LENGTH: 21
<212> TYPE: DNA
<213> ORGANISM: Homo sapiens

<400> SEQUENCE: 31
gaggagacct gggtggctag a                                                 21

<210> SEQ ID NO 32
<211> LENGTH: 22
<212> TYPE: DNA
<213> ORGANISM: Homo sapiens

<400> SEQUENCE: 32
gtgcaagcac cattattccc tc                                                22

<210> SEQ ID NO 33
<211> LENGTH: 22
<212> TYPE: DNA
```

-continued

```
<213> ORGANISM: Homo sapiens

<400> SEQUENCE: 33
gacagagggc agatccatga ag                                       22

<210> SEQ ID NO 34
<211> LENGTH: 22
<212> TYPE: DNA
<213> ORGANISM: Homo sapiens

<400> SEQUENCE: 34
ccaggcactg aaataactca cc                                       22

<210> SEQ ID NO 35
<211> LENGTH: 24
<212> TYPE: DNA
<213> ORGANISM: Homo sapiens

<400> SEQUENCE: 35
gggataagac atcgaatgtt caca                                     24

<210> SEQ ID NO 36
<211> LENGTH: 24
<212> TYPE: DNA
<213> ORGANISM: Homo sapiens

<400> SEQUENCE: 36
taacatccag ggatctagtt ctga                                     24

<210> SEQ ID NO 37
<211> LENGTH: 24
<212> TYPE: DNA
<213> ORGANISM: Homo sapiens

<400> SEQUENCE: 37
ttaaagctac agagcattca ttca                                     24

<210> SEQ ID NO 38
<211> LENGTH: 24
<212> TYPE: DNA
<213> ORGANISM: Homo sapiens

<400> SEQUENCE: 38
tttcactcag aatttgcata atcc                                     24

<210> SEQ ID NO 39
<211> LENGTH: 22
<212> TYPE: DNA
<213> ORGANISM: Homo sapiens

<400> SEQUENCE: 39
tgagtttcta tgagggagcc ag                                       22

<210> SEQ ID NO 40
<211> LENGTH: 22
<212> TYPE: DNA
<213> ORGANISM: Homo sapiens

<400> SEQUENCE: 40
tgccaggcac tcttctaggc at                                       22

<210> SEQ ID NO 41
<211> LENGTH: 22
```

-continued

```
<212> TYPE: DNA
<213> ORGANISM: Homo sapiens

<400> SEQUENCE: 41
agagtcgaga aaggaagagc ca                                              22

<210> SEQ ID NO 42
<211> LENGTH: 22
<212> TYPE: DNA
<213> ORGANISM: Homo sapiens

<400> SEQUENCE: 42
taagcctgaa ccctagcact tg                                              22

<210> SEQ ID NO 43
<211> LENGTH: 24
<212> TYPE: DNA
<213> ORGANISM: Homo sapiens

<400> SEQUENCE: 43
tatacagaat caccttgaca aact                                            24

<210> SEQ ID NO 44
<211> LENGTH: 23
<212> TYPE: DNA
<213> ORGANISM: Homo sapiens

<400> SEQUENCE: 44
gtacataata tgtgctgagt gct                                             23

<210> SEQ ID NO 45
<211> LENGTH: 25
<212> TYPE: DNA
<213> ORGANISM: Homo sapiens

<400> SEQUENCE: 45
ataattactt gagagatatt ggata                                           25

<210> SEQ ID NO 46
<211> LENGTH: 24
<212> TYPE: DNA
<213> ORGANISM: Homo sapiens

<400> SEQUENCE: 46
attaaacctc aagcatagct tcta                                            24

<210> SEQ ID NO 47
<211> LENGTH: 20
<212> TYPE: DNA
<213> ORGANISM: Homo sapiens

<400> SEQUENCE: 47
ccatttgcaa ggtttctccc                                                 20

<210> SEQ ID NO 48
<211> LENGTH: 22
<212> TYPE: DNA
<213> ORGANISM: Homo sapiens

<400> SEQUENCE: 48
aatccttttc atggtgagca tt                                              22

<210> SEQ ID NO 49
```

```
<211> LENGTH: 21
<212> TYPE: DNA
<213> ORGANISM: Homo sapiens

<400> SEQUENCE: 49
ttgataccat ttgatgtgcc t                                              21

<210> SEQ ID NO 50
<211> LENGTH: 21
<212> TYPE: DNA
<213> ORGANISM: Homo sapiens

<400> SEQUENCE: 50
gttgattttc gtgtttgagg c                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence:sequencing
      primer

<400> SEQUENCE: 51
gtcagatgat acaaaaggac a                                              21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:sequencing
      primer

<400> SEQUENCE: 52
tgaaaggctg ggacactgct                                                20

<210> SEQ ID NO 53
<211> LENGTH: 20
<212> TYPE: DNA
<213> ORGANISM: Homo sapiens

<400> SEQUENCE: 53
ttcatgaaag gtgaggagca                                                20

<210> SEQ ID NO 54
<211> LENGTH: 20
<212> TYPE: DNA
<213> ORGANISM: Homo sapiens

<400> SEQUENCE: 54
tgtctttcag atcggttata                                                20

<210> SEQ ID NO 55
<211> LENGTH: 20
<212> TYPE: DNA
<213> ORGANISM: Homo sapiens

<400> SEQUENCE: 55
tctatgaaaa gtaagtttat                                                20

<210> SEQ ID NO 56
<211> LENGTH: 20
<212> TYPE: DNA
<213> ORGANISM: Homo sapiens
```

```
<400> SEQUENCE: 56
tgtatcttag tttctatgca                                          20

<210> SEQ ID NO 57
<211> LENGTH: 20
<212> TYPE: DNA
<213> ORGANISM: Homo sapiens

<400> SEQUENCE: 57
gaaactaaaa gtgagtattg                                          20

<210> SEQ ID NO 58
<211> LENGTH: 20
<212> TYPE: DNA
<213> ORGANISM: Homo sapiens

<400> SEQUENCE: 58
ctctttctag tcatacagtt                                          20

<210> SEQ ID NO 59
<211> LENGTH: 20
<212> TYPE: DNA
<213> ORGANISM: Homo sapiens

<400> SEQUENCE: 59
tgcctatgca gtaagtacct                                          20

<210> SEQ ID NO 60
<211> LENGTH: 20
<212> TYPE: DNA
<213> ORGANISM: Homo sapiens

<400> SEQUENCE: 60
tctgtcttag gtaatctatt                                          20

<210> SEQ ID NO 61
<211> LENGTH: 20
<212> TYPE: DNA
<213> ORGANISM: Homo sapiens

<400> SEQUENCE: 61
ttccattcag gtataactcc                                          20

<210> SEQ ID NO 62
<211> LENGTH: 20
<212> TYPE: DNA
<213> ORGANISM: Homo sapiens

<400> SEQUENCE: 62
atgtttatag ggatgcttcc                                          20

<210> SEQ ID NO 63
<211> LENGTH: 20
<212> TYPE: DNA
<213> ORGANISM: Homo sapiens

<400> SEQUENCE: 63
aatcagaaag gtaataacaa                                          20

<210> SEQ ID NO 64
<211> LENGTH: 20
<212> TYPE: DNA
```

```
<213> ORGANISM: Homo sapiens

<400> SEQUENCE: 64
ctgcttttag ggattacaac                                           20

<210> SEQ ID NO 65
<211> LENGTH: 20
<212> TYPE: DNA
<213> ORGANISM: Homo sapiens

<400> SEQUENCE: 65
acattatgag gtttgtacat                                           20

<210> SEQ ID NO 66
<211> LENGTH: 20
<212> TYPE: DNA
<213> ORGANISM: Homo sapiens

<400> SEQUENCE: 66
attctgccag cgagttgaaa                                           20

<210> SEQ ID NO 67
<211> LENGTH: 20
<212> TYPE: DNA
<213> ORGANISM: Homo sapiens

<400> SEQUENCE: 67
attgagaatg gtaggttttt                                           20

<210> SEQ ID NO 68
<211> LENGTH: 20
<212> TYPE: DNA
<213> ORGANISM: Homo sapiens

<400> SEQUENCE: 68
gttcctttag gttatcctct                                           20

<210> SEQ ID NO 69
<211> LENGTH: 20
<212> TYPE: DNA
<213> ORGANISM: Homo sapiens

<400> SEQUENCE: 69
cactgcaaag gtgtgtgcaa                                           20

<210> SEQ ID NO 70
<211> LENGTH: 20
<212> TYPE: DNA
<213> ORGANISM: Homo sapiens

<400> SEQUENCE: 70
tctcttacag ctggtcttgg                                           20

<210> SEQ ID NO 71
<211> LENGTH: 20
<212> TYPE: DNA
<213> ORGANISM: Homo sapiens

<400> SEQUENCE: 71
tcctggaaga gtaagtatat                                           20

<210> SEQ ID NO 72
<211> LENGTH: 20
```

```
<212> TYPE: DNA
<213> ORGANISM: Homo sapiens

<400> SEQUENCE: 72
tattatacag aaagcaagca                                                  20

<210> SEQ ID NO 73
<211> LENGTH: 20
<212> TYPE: DNA
<213> ORGANISM: Homo sapiens

<400> SEQUENCE: 73
atttggagag gtaagtcttc                                                  20

<210> SEQ ID NO 74
<211> LENGTH: 20
<212> TYPE: DNA
<213> ORGANISM: Homo sapiens

<400> SEQUENCE: 74 tttttttccag gataacttag                                                 20

<210> SEQ ID NO 75
<211> LENGTH: 20
<212> TYPE: DNA
<213> ORGANISM: Homo sapiens

<400> SEQUENCE: 75
gtgcatttag gtagatctgt                                                  20

<210> SEQ ID NO 76
<211> LENGTH: 20
<212> TYPE: DNA
<213> ORGANISM: Homo sapiens

<400> SEQUENCE: 76
gtgcatttag gtcagatgat                                                  20

<210> SEQ ID NO 77
<211> LENGTH: 20
<212> TYPE: DNA
<213> ORGANISM: Homo sapiens

<400> SEQUENCE: 77
agcctttcag gtactgccaa                                                  20

<210> SEQ ID NO 78
<211> LENGTH: 20
<212> TYPE: DNA
<213> ORGANISM: Homo sapiens

<400> SEQUENCE: 78
ctccgcaaag attaagttca                                                  20

<210> SEQ ID NO 79
<211> LENGTH: 20
<212> TYPE: DNA
<213> ORGANISM: Homo sapiens

<400> SEQUENCE: 79
ctgtaagaag gtaattttc                                                   20

<210> SEQ ID NO 80
```

-continued

```
<211> LENGTH: 20
<212> TYPE: DNA
<213> ORGANISM: Homo sapiens

<400> SEQUENCE: 80
ttccattcag cttttccata                                              20

<210> SEQ ID NO 81
<211> LENGTH: 20
<212> TYPE: DNA
<213> ORGANISM: Homo sapiens

<400> SEQUENCE: 81
ttctatccct gtaagtgcgc                                              20

<210> SEQ ID NO 82
<211> LENGTH: 20
<212> TYPE: DNA
<213> ORGANISM: Homo sapiens

<400> SEQUENCE: 82
ccctgcacag tcccttcagt                                              20
```

HUMAN CDC14A GENE

CROSS-REFERENCE TO RELATED APPLICATION

The present application claims the benefit of U.S. provisional application Ser. No. 60/113,833 filed on Dec. 23, 1998, incorporated herein by reference.

FIELD OF THE INVENTION

The present invention relates generally to the field of human genetics. Specifically, the present invention relates to human CDC14A gene which has been found to be mutated in certain tumor cell lines. More specifically, the invention relates to a novel sequence for the human CDC14A gene. The present invention further relates to somatic mutations in the CDC14A gene in human cancer and their use in the diagnosis and prognosis of human cancer. The invention also relates to the therapy of human cancers which have a mutation in the CDC14A gene, including gene therapy, protein replacement therapy and protein mimetics. The invention further relates to the screening of drugs for cancer therapy. Finally, the invention relates to the screening of the CDC14A gene for mutations, which are useful for diagnosing the predisposition to cancer.

The publications and other materials used herein to illuminate the background of the invention, and in particular, cases to provide additional details respecting the practice, are incorporated herein by reference, and for convenience, are referenced by author and date in the following text and respectively grouped in the appended List of References.

BACKGROUND OF THE INVENTION

Tumorigenesis is a multistep process that involves loss of function in tumor suppressor genes and gain of function in oncogenes. Genetic and molecular studies in the past several years have contributed significantly to the identification and isolation of numerous tumor suppressor genes from many types of cancer (Brown and Solomon, 1997). Characterization of these genes have revealed that the products they encode participate in a variety of biochemical pathways including cell cycle regulation, cell adhesion, DNA repair, transcription, RNA processing, apoptosis, and signal transduction.

It is well established that some protein kinases acting as oncoproteins in signal transduction pathways perturb normal cell growth and cell proliferation. An excessive increase in phosphorylation activity is one mechanism by which a cell is transformed. Phosphatases are proteins that antagonize the phosphorylation activities of kinases, hence they have been postulated to suppress cancer development (Parsons, 1998). The role of a phosphatase as a tumor suppressor in cancer has not been documented until the recent discovery of MMAC1/PTEN and PPP2R1B (Steck et al, 1997; Li et al, 1997; Wang et al, 1998). The MMAC1/PTEN gene encodes a dual-specificity phosphatase that appears to be involved in signal transduction by dephosphorylating phosphatidylinositol 3,4,5-triphosphate, a lipid component that is involved in cell growth signaling (Maehama and Dixon, 1998). Its loss of function is associated with a wide spectrum of human tumor types including glioma, carcinoma of breast, prostate and endometrium. PPP2R1B gene encodes the beta isoform of the A subunit of serine/threonine protein phosphatase 2A that is mutated in human lung and colon tumors (Wang et al, 1998). Its putative tumor suppressor activity may be exerted through cell cycle regulation or cell growth control. On contrary to the tumor suppression function of MMAC1/PTEN and PPP2R1B, another class of phosphatases, CDC25A and B, have been shown to be oncogenic (Galaktionov et al, 1995). A function of CDC25 is to activate cyclin-dependent kinases which are positive effectors of cell growth. Overexpression of CDC25B have been detected in primary breast cancer (Galaktionov et al, 1995).

It has been amply demonstrated that different members of the same tumor suppressor gene family are targeted for mutation during cancer development. For examples, TP53 and p51 in the p53 family (Osada et al, 1998); RB and p130 in the retinoblastoma family (Helin et al, 1997); Smad 2 and 4 in the Smad family (Eppert et al, 1996; Hahn et al, 1996; Howe et al, 1998); cadE and cadH in the cadherin family (Miki et al, 1997; Hiraguri et al, 1998; Guilford et al, 1998; Sato et al, 1998) are mutated in either primary tumors or tumor cell lines. It is therefore plausible that members in the MMAC1/PTEN phosphatase gene family may be targeted. Recently a human homolog to yeast CDC14 has been cloned and shown to share homology with the phosphatase domain and ser/thr rich C-terminal domain of MMAC1/PTEN (Li et al, 1997). Human CDC14 A is a dual-specificity phosphatase which can functionally complement a yeast strain that carries a cdc14-1$^{ts}$ allele (Li et al, 1997). Under certain conditions, human MMAC1/PTEN can also complement the same yeast temperature sensitive strain (Li et al, 1997). A similarity in structural and functional relationship implies that these phosphatases may target common substrates that are involved in the process of tumor suppression.

Loss of tumor suppressor gene activity could occur through a number of mechanisms, such as homozygous deletions, point or frameshift mutations, or loss of expression. We examined a panel of 138 tumor cell lines for homozygous deletions and sequence alterations in the CDC14 A gene. We have identified an acceptor splice site mutation that causes deletion of exon 13 in the breast cell line MDA-MB-436.

SUMMARY OF THE INVENTION

The present invention relates generally to the field of human genetics. Specifically, the present invention relates to human CDC14A gene which has been found to be mutated in certain tumor cell lines. More specifically, the invention relates to a novel sequence for the human CDC14A gene. The present invention further relates to somatic mutations in the CDC14A gene in human cancer and their use in the diagnosis and prognosis of human cancer. The invention also relates to the therapy of human cancers which have a mutation in the CDC14A gene, including gene therapy, protein replacement therapy and protein mimetics. The invention further relates to the screening of drugs for cancer therapy. Finally, the invention relates to the screening of the CDC14A gene for mutations, which are useful for diagnosing the predisposition to cancer.

SUMMARY OF SEQUENCE LISTING

Figure 1:
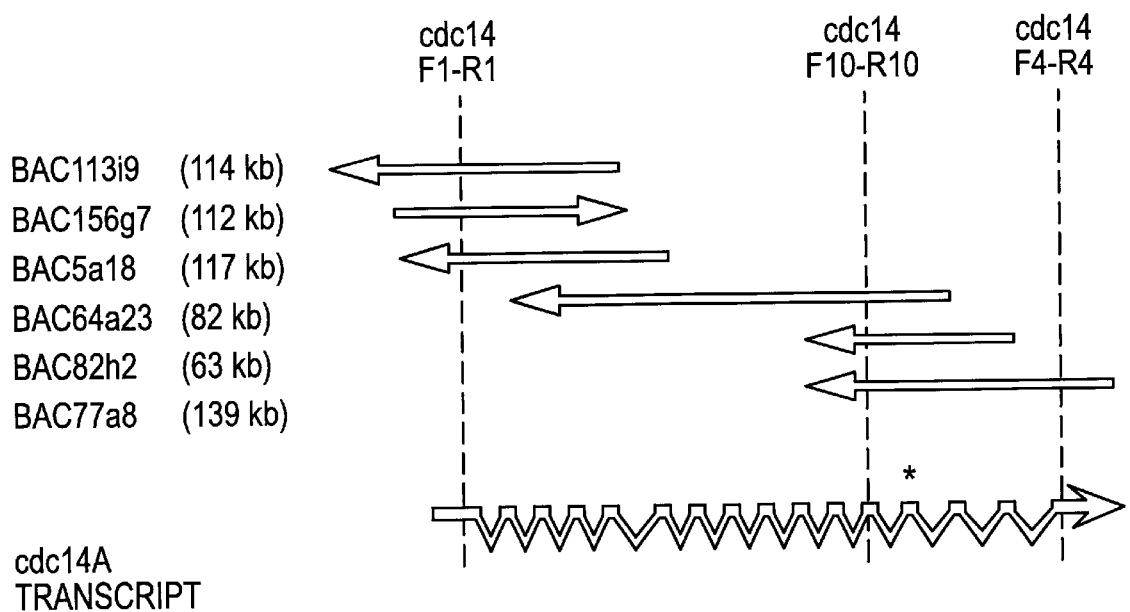
FIG. 1 is a contig map of six overlapping BACs covering the entire coding region of CDC14A. STS primers cdc14.F1-R1, F4-R4, F10-R10 were used for BAC library screening by PCR. Size of each BAC is as indicated. Relative position of each exon is shown but not to scale.

SEQ ID NO:1 is the nucleotide sequence for the human CDC14A cDNA from the start codon through the stop codon. SEQ ID NO:2 is the amino acid sequence for the human CDC14A protein. SEQ ID NO:3 to SEQ ID NO:22 are the sequences of primers for the coding region. SEQ ID NO:23 to SEQ ID NO:50 are the sequences of primers for the genomic region. SEQ ID NO:51 and SEQ ID NO:52 are sequencing primers. SEQ ID NO:53 to SEQ ID NO:82 are 5' donor and 3' acceptor splice site junctions for each exon of the CDC14A gene.

DETAILED DESCRIPTION OF THE INVENTION

The present invention provides an isolated polynucleotide comprising all, or a portion of the CDC14A locus or of a mutated CDC14A locus, preferably at least eight bases and not more than about 27 kb in length. Such polynucleotides may be antisense polynucleotides. The present invention also provides a recombinant construct comprising such an isolated polynucleotide, for example, a recombinant construct suitable for expression in a transformed host cell.

Also provided by the present invention are methods of detecting a polynucleotide comprising a portion of the CDC14A locus or its expression product in an analyte. Such methods may further comprise the step of amplifying the portion of the CDC14A locus, and may further include a step of providing a set of polynucleotides which are primers for amplification of said portion of the CDC14A locus. The method is useful for either diagnosis of the predisposition to cancer or the diagnosis or prognosis of cancer.

The present invention also provides isolated antibodies, preferably monoclonal antibodies, which specifically bind to an isolated polypeptide comprised of at least five amino acid residues encoded by the CDC14A locus.

The present invention also provides kits for detecting in an analyte a polynucleotide comprising a portion of the CDC14A locus, the kits comprising a polynucleotide complementary to the portion of the CDC14A locus packaged in a suitable container, and instructions for its use.

The present invention further provides methods of preparing a polynucleotide comprising polymerizing nucleotides to yield a sequence comprised of at least eight consecutive nucleotides of the CDC14A locus; and methods of preparing a polypeptide comprising polymerizing amino acids to yield a sequence comprising at least five amino acids encoded within the CDC14A locus.

The present invention further provides methods of screening the CDC14A gene to identify mutations. Such methods may further comprise the step of amplifying a portion of the CDC14A locus, and may further include a step of providing a set of polynucleotides which are primers for amplification of said portion of the CDC14A locus. Such methods may also include a step of providing the complete set of short polynucleotides defined by the sequence of CDC14A or discrete subsets of that sequence, all single-base substitutions of that sequence or discrete subsets of that sequence, all 1-, 2-, 3-, or 4-base deletions of that sequence or discrete subsets of that sequence, and all 1-, 2-, 3-, or 4-base insertions in that sequence or discrete subsets of that sequence. The method is useful for identifying mutations for use in either diagnosis of the predisposition to cancer or the diagnosis or prognosis of cancer.

The present invention further provides methods of screening suspected CDC14A mutant alleles to identify mutations in the CDC14A gene.

In addition, the present invention provides methods to screen drugs for inhibition or restoration of CDC14A gene product function as an anticancer therapy.

Finally, the present invention provides the means necessary for production of gene-based therapies directed at cancer cells. These therapeutic agents may take the form of polynucleotides comprising all or a portion of the CDC14A locus placed in appropriate vectors or delivered to target cells in more direct ways such that the function of the CDC14A protein is reconstituted. Therapeutic agents may also take the form of polypeptides based on either a portion of, or the entire protein sequence of CDC14A. These may functionally replace the activity of CDC14A in vivo.

It is a discovery of the present invention that the CDC14A locus is mutated in cancer cell lines. The CDC14A gene disclosed herein encodes a CDC14A protein, which has been found to be non-identical to publicly available protein or cDNA sequences. It is a discovery of the present invention that mutations in the CDC14A locus in the germline are indicative of a predisposition to cancer. The mutational events of the CDC14A locus can involve deletions, insertions and nucleotide substitutions within the coding sequence and the non-coding sequence.

Human CDC14A is a dual-specificity phosphatase which shares similarity with the recently identified tumor suppressor MMAC1/PTEN. We hypothesize that homologs in the phosphatase gene family may be targeted for mutation during tumorigenesis. By radiation hyrid mapping, we localize CDC14A to chromosome 1p, a region that has been shown to exhibit loss of heterozygosity in certain types of tumors. Screening of a panel of 138 cDNAs from tumor cell lines for coding mutations, we identify a 48 bp in-frame deletion in the cDNA of the breast cell line MDA-MB-436. Further, by mapping the exon/intron structure of the CDC14A gene, we show definitively the deletion is the result of an acceptor splice site mutation at exon 13 in the genome. The invariant AG was converted to AT. The accompanying loss of expression of the wild type allele in the same breast cell line reinforces the possibility that CDC14A may be a tumor suppressor, perhaps exerting its effect at the cell cycle.

The choice of using tumor cell line cDNA templates as a preliminary screening sample set for our candidate gene approach is based on our previous success in identifying p16 and MKK4 as tumor suppressor candidates with a similar strategy (Kamb et al, 1994; Teng et al, 1997). The generally accepted theory of tumorigenesis is that multiple sets of genes have undergone mutagenesis to give cell lines a selective growth advantage. Once established, these bonafide mutations remain a permanent feature of the tumor cell lines, thus providing an useful resource for mutation screening. In our previous analysis of the MKK4 gene, we had initially showed that it was mutated in breast and pancreatic tumor cell lines but at a very low frequency (Teng et al, 1997). Subsequently, in a more comprehensive screen with primary breast tumors and pancreatic xenografts, somatic mutations including homozygous deletions were identified (Su et al, 1998), thus validating the tumor cell line screening approach as an useful strategy to identify some cancer gene candidates.

Useful Diagnostic Techniques

According to the diagnostic and prognostic method of the present invention, alteration of the wild-type CDC14A locus is detected. In addition, the method can be performed by detecting the wild-type CDC14A locus and confirming the lack of a predisposition to cancer at the CDC14A locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues, e.g., in the tumor tissue, and are not inherited in the germline. Germline mutations can be found in any of a body's tissues and are inherited. If only a single allele is somatically mutated, an early neoplastic state is indicated. However, if both alleles are somatically mutated, then a late neoplastic state is indicated. The finding of CDC14A mutations thus provides both diagnostic and prognostic information. An CDC14A allele which is not deleted (e.g., found on the sister chromosome to a chromosome carrying an CDC14A deletion) can be screened for other mutations, such as insertions, small deletions, and point mutations. It is believed that many mutations found in tumor tissues will be those leading to decreased expression of the CDC14A gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to reduction or loss of expression of the CDC14A gene product, expression of an altered CDC14A gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

Predisposition to cancers, such as the cancers identified herein, can be ascertained by testing any tissue of a human for mutations of the CDC14A gene. For example, a person who has inherited a germline CDC14A mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the CDC14A gene. Similarly, tumor tissue or cells can also be screened to determine whether CDC14A is involved in the neoplastic condition of the tissue or cells. Alteration of a wild-type CDC14A allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. For a gene, such as CDC14A, manual sequencing is can be very labor-intensive, but under optimal conditions, mutations in the coding sequence of a gene are rarely missed. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

In order to detect the alteration of the wild-type CDC14A gene in a tissue, it is helpful to isolate the tissue free from surrounding normal tissues. Means for enriching tissue preparation for tumor cells are known in the art. For example, the tissue may be isolated from paraffin or cryostat sections. Cancer cells may also be separated from normal cells by flow cytometry. These techniques, as well as other techniques for separating tumor cells from normal cells, are well known in the art. If the tumor tissue is highly contaminated with normal cells, detection of mutations is more difficult.

Detection of point mutations may be accomplished by molecular cloning of the CDC14A allele(s) and sequencing the allele(s) using techniques well known in the art. Alternatively, the gene sequences can be amplified directly from a genomic DNA preparation from the tumor tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to a particular CDC14A mutation. If the particular CDC14A mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the CDC14A mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type CDC14A gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the CDC14A mRNA or gene but can be a segment of either. If the riboprobe comprises only a segment of the CDC14A mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the CDC14A gene can also be detected using Southern hybridization, especially if the changes are gross rearrangements, such as deletions and insertions.

DNA sequences of the CDC14A gene which have been amplified by use of PCR may also be screened using allele-specific probes. These probes are nucleic acid oligomers, each of which contains a region of the CDC14A gene sequence harboring a known mutation. For example, one oligomer may be about 30 nucleotides in length (although shorter and longer oligomers are also usable as well recognized by those of skill in the art), corresponding to a portion of the CDC14A gene sequence. By use of a battery of such allele-specific probes, PCR amplification products can be screened to identify the presence of a previously identified mutation in the CDC14A gene. Hybridization of allele-specific probes with amplified CDC14A sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic CDC14A sequences from cancer patients with those from a control population. Alternatively, one could sequence messenger RNA after amplification, e.g., by PCR, thereby eliminating the necessity of determining the exon structure of the candidate gene.

Mutations from cancer patients falling outside the coding region of CDC14A can be detected by examining the non-coding regions, such as introns and regulatory sequences near or within the CDC14A gene. An early indication that mutations in noncoding regions are important may come from Northern blot experiments that reveal messenger RNA molecules of abnormal size or abundance in cancer patients as compared to control individuals.

Alteration of CDC14A mRNA expression can be detected by any techniques known in the art. These include Northern blot analysis, PCR amplification and RNase protection. Diminished mRNA expression indicates an alteration of the wild-type CDC14A gene. Alteration of wild-type CDC14A genes can also be detected by screening for alteration of wild-type CDC14A protein. For example, monoclonal antibodies immunoreactive with CDC14A can be used to screen a tissue. Lack of cognate antigen would indicate an CDC14A mutation. Antibodies specific for products of mutant alleles could also be used to detect mutant CDC14A gene product. Such immunological assays can be done in any convenient formats known in the art. These include Western blots, immunohistochemical assays and ELISA assays. Any means for detecting an altered CDC14A protein can be used to detect alteration of wild-type CDC14A genes. Functional assays, such as protein binding determinations, can be used. In addition, assays can be used which detect CDC14A biochemical function. Finding a mutant CDC14A gene product indicates alteration of a wild-type CDC14A gene.

Mutant CDC14A genes or gene products can also be detected in other human body samples, such as serum, stool, urine and sputum. The same techniques discussed above for detection of mutant CDC14A genes or gene products in tissues can be applied to other body samples. Cancer cells are sloughed off from tumors and appear in such body samples. In addition, the CDC14A gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant CDC14A genes or gene products.

The methods of diagnosis of the present invention are applicable to any tumor in which CDC14A has a role in tumorigenesis. The diagnostic method of the present invention is useful for clinicians, so they can decide upon an appropriate course of treatment.

The primer pairs of the present invention are useful for determination of the nucleotide sequence of a particular CDC14A allele using PCR. The pairs of single-stranded DNA primers can be annealed to sequences within or surrounding the CDC14A gene on chromosome 1 in order to prime amplifying DNA synthesis of the CDC14A gene itself. A complete set of these primers allows synthesis of all of the nucleotides of the CDC14A gene coding sequences, i.e., the exons. Examples of suitable primers are described herein. Other suitable primers can be readily designed by a person with skill in the art. The set of primers preferably allows synthesis of both intron and exon sequences. Allele-specific primers can also be used. Such primers anneal only to particular CDC14A mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from CDC14A sequences or sequences adjacent to CDC14A, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of the CDC14A open reading frame shown in SEQ ID NO:1, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the CDC14A gene or mRNA using other techniques.

It has been discovered that individuals with the wild-type CDC14A gene do not have cancer which results from the CDC14A allele. However, mutations which interfere with the function of the CDC14A protein are involved in the pathogenesis of cancer. Thus, the presence of an altered (or a mutant) CDC14A gene which produces a protein having a loss of function, or altered function, directly correlates to an increased risk of cancer. In order to detect an CDC14A gene mutation, a biological sample is prepared and analyzed for a difference between the sequence of the CDC14A allele being analyzed and the sequence of the wild-type CDC14A allele. Mutant CDC14A alleles can be initially identified by any of the techniques described above. The mutant alleles are then sequenced to identify the specific mutation of the particular mutant allele. Alternatively, mutant CDC14A alleles can be initially identified by identifying mutant (altered) CDC14A proteins, using conventional techniques. The mutant alleles are then sequenced to identify the specific mutation for each allele. The mutations, especially those which lead to an altered function of the CDC14A protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); and Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the CDC14A region are preferably complementary to, and hybridize specifically to sequences in the CDC14A region or in regions that flank a target region therein. CDC14A sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the CDC14A polypeptides and fragments thereof or to polynucleotide sequences from the CDC14A region, particularly from the CDC14A locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the CDC14A polypeptide or fragment. Monoclonal antibodies may be made by injecting mice with the protein polypeptides, fusion proteins or fragments thereof. Monoclonal antibodies will be screened by ELISA and tested for specific immunoreactivity with CDC14A polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ M$^{-1}$ or preferably $10^{-9}$ to $10^{-10}$ M$^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., a two-hybrid screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

As used herein, the terms "diagnosing" or "prognosing," as used in the context of neoplasia, are used to indicate 1) the classification of lesions as neoplasia, 2) the determination of the severity of the neoplasia, or 3) the monitoring of the disease progression, prior to, during and after treatment.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"CDC14A Allele" refers to normal alleles of the CDC14A locus as well as alleles carrying variations that predispose individuals to develop prostate cancer. Such predisposing alleles are also called "CDC14A susceptibility alleles".

"CDC14A Locus", "CDC14A Gene", "CDC14A Nucleic Acids" or "CDC14A Polynucleotide" each refer to polynucleotides, all of which are in the CDC14A region, that are likely to be expressed in normal tissue, certain alleles of which predispose an individual to develop prostate cancers. Mutations at the CDC14A locus may be involved in the initiation and/or progression of other types of tumors. The locus is indicated in part by mutations that predispose individuals to develop cancer. These mutations fall within the CDC14A region described infra. The CDC14A locus is intended to include coding sequences, intervening sequences and regulatory elements controlling transcription and/or translation. The CDC14A locus is intended to include all allelic variations of the DNA sequence.

These terms, when applied to a nucleic acid, refer to a nucleic acid which encodes an CDC14A polypeptide, fragment, homolog or variant, including, e.g., protein fusions or deletions. The nucleic acids of the present invention will possess a sequence which is either derived from, or substantially similar to a natural CDC14A-encoding gene or one having substantial homology with a natural CDC14A-encoding gene or a portion thereof.

The CDC14A gene or nucleic acid includes normal alleles of the CDC14A gene, including silent alleles having no effect on the amino acid sequence of the CDC14A polypeptide as well as alleles leading to amino acid sequence variants of the CDC14A polypeptide that do not substantially affect its function. These terms also include alleles having one or more mutations which adversely affect the function of the CDC14A polypeptide. A mutation may be a change in the CDC14A nucleic acid sequence which produces a deleterious change in the amino acid sequence of the CDC14A polypeptide, resulting in partial or complete loss of CDC14A function, or may be a change in the nucleic acid sequence which results in the loss of effective CDC14A expression or the production of aberrant forms of the CDC14A polypeptide.

The CDC14A nucleic acid may be that shown in SEQ ID NO:1 or it may be an allele as described above or a variant or derivative differing from that shown by a change which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NO:1 yet encode a polypeptide with the same amino acid sequence as shown in SEQ ID NO:2. That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NO:2. Nucleic acid encoding a polypeptide which is an amino acid sequence variant, derivative or allele of the amino acid sequence shown in SEQ ID NO:2 is also provided by the present invention.

The CDC14A gene also refers to (a) any DNA sequence that (i) hybridizes to the complement of the DNA sequences that encode the amino acid sequence set forth in SEQ ID NO:2 under highly stringent conditions (Ausubel et al., 1992) and (ii) encodes a gene product functionally equivalent to CDC14A, or (b) any DNA sequence that (i) hybridizes to the complement of the DNA sequences that encode the amino acid sequence set forth in SEQ ID NO:2 under less stringent conditions, such as moderately stringent conditions (Ausubel et al., 1992) and (ii) encodes a gene product functionally equivalent to CDC14A. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the CDC14A region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an CDC14A-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega Biotec, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

"CDC14A Region" refers to a portion of human chromosome 1 at or near band 1p21 which is 2.22 cR telomeric to the Whitehead marker WI-3294.

As used herein, the terms "CDC14A locus", "CDC14A allele" and "CDC14A region" all refer to the double-stranded DNA comprising the locus, allele, or region, as well as either of the single-stranded DNAs comprising the locus, allele or region.

As used herein, a "portion" of the CDC14A locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from any of SEQ ID NOs:1 or 3–82, its complement or functionally equivalent nucleic acid sequences. The present invention does not include nucleic acids which exist in the prior art. That is, the present invention includes all nucleic acids having at least 8 nucleotides derived from any of SEQ ID NOs:1 or 3–82 with the proviso that it does not include nucleic acids existing in the prior art.

"CDC14A protein" or "CDC14A polypeptide" refers to a protein or polypeptide encoded by the CDC14A locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native CDC14A sequence, preferably in excess of about 90%, and more preferably at least about 95% homologous. Also included are proteins encoded by DNA which hybridize under high or low stringency conditions, to CDC14A-encoding nucleic acids and closely related polypeptides or proteins retrieved by antisera to the CDC14A protein(s).

An CDC14A polypeptide may be that derived from any of the exons described herein which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of an CDC14A polypeptide. Such polypeptides may have an amino acid sequence which differs from that derived from any of the exons described herein by one or more of addition, substitution, deletion or insertion of one or more amino acids. Preferred such polypeptides have CDC14A function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an CDC14A polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of an CDC14A polypeptide. A peptide mimetic may be a peptidecontaining molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of a natural CDC14A polypeptide.

"Probes". Polynucleotide polymorphisms associated with CDC14A alleles which predispose to certain cancers or are associated with most cancers are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of an CDC14A susceptibility allele. An example of high stringency conditions is to hybridize to filer bound DNA in 0.5 M $NaHPO_4$, 7% sodium dodecyl sulfate (SDS), 1 mM EDTA at 65° C. and to wash in 0.1×SSC/0.1% SDS at 68° C. (Ausubel et al., 1992). Less stringent conditions, such as moderately stringent conditions, are defined as above but with the wash step being in 0.2×SSC/0.1% SDS at 42° C.

Probes for CDC14A alleles may be derived from the sequences of the CDC14A region, its cDNA, functionally equivalent sequences, or the complements thereof. The probes may be of any suitable length, which span all or a portion of the CDC14A region, and which allow specific hybridization to the CDC14A region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al, 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding CDC14A are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding CDC14A is present in a cell or tissue. The present invention includes all novel probes having at least 8 nucleotides derived from any of SEQ ID NOs:1 or 3–82, their complement or functionally equivalent nucleic acid sequences. The present invention does not include probes which exist in the prior art. That is, the present invention includes all probes having at least 8 nucleotides derived from any of SEQ ID NOs:1 or 3–82 with the proviso that they do not include probes existing in the prior art.

Similar considerations and nucleotide lengths are also applicable to primers which may be used for the amplification of all or part of the CDC14A gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding CDC14A is present in a cell or tissue. The present invention includes all novel primers having at least 8 nucleotides derived from the CDC14A locus for amplifying the CDC14A gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for CDC14A polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of CDC14A polypeptides. Immunological activities include both immunogenic function in a target immune system, as well as sharing of immunological epitopes for binding, serving as either a competitor or substitute antigen for an epitope of the CDC14A protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for CDC14A polypeptides or fragments thereof is described below.

The present invention also provides for fusion polypeptides, comprising CDC14A polypeptides and fragments. Homologous polypeptides may be fusions between two or more CDC14A polypeptide sequences or between the sequences of CDC14A and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski etal., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the CDC14A polypeptides from other biological material, such as from cells transformed with recombinant nucleic acids encoding CDC14A, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

An CDC14A protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Identity means the degree of sequence relatedness between two polypeptide or two polynucleotides sequences as determined by the identity of the match between two strings of such sequences. Identity can be readily calculated. While there exist a number of methods to measure identity between two polynucleotide or polypeptide sequences, the term "identity" is well known to skilled artisans (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D. (1988). Preferred methods to determine identity are designed to give the largest match between the two sequences tested. Such methods are codified in computer programs. Preferred computer program methods to determine identity between two sequences include, but are not limited to, GCG program package (Devereux et al. (1984), BLASTP, BLASTN, FASTA (Altschul et al. (1990); Altschul et al. (1997)).

Alternatively, substantial homology or similarity exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705, as well as the software described above with reference to nucleic acid homology. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type CDC14A nucleic acid or wild-type CDC14A polypeptide. The modified polypeptide will be substantially homologous to the wild-type CDC14A polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type CDC14A polypeptide. Alternatively, the similarity of function (activity) of the modified polypeptide may be higher than the activity of the wild-type CDC14A polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CDC14A gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, e.g., in Sambrook et al., 1989 or Ausubel et al., 1992.

The polynucleotides of the present invention may also be produced by chemical synthesis, e.g., by the phosphoramidite method described by Beaucage and Caruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native CDC14A protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 or Ausubel et al. 1992.

An appropriate promoter and other necessary vector sequences will be selected so as to be functional in the host, and may include, when appropriate, those naturally associated with CDC14A genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Moloney leukemia virus, mouse tumor virus, avian sarcoma viruses, adenovirus II, bovine papilloma virus or polyoma. Insection promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art. Alternatively, they may replicate by being transfected into helper cells or being co-transfected with a helper vector.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the CDC14A nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan, 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of CDC14A polypeptides.

The CDC14A gene products can also be expressed in transgenic animals. Animals of any species, including, but not limited to, mice, rats, rabbits, guinea pigs, pigs, micropigs, goats and non-human primates, e.g., baboons, monkeys and chimpanzees, may be used to generate CDC14A transgenic animals.

Any technique known in the art may be used to introduce the CDC14A gene transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., 1985); gene targeting in embryonic stem cells (Thompson et al., 1989); electroporation of embryos (Lo, 1983); and sperm-mediated gene transfer (Lavitrano et al., 1989); etc. For a review of such techniques, see Gordon (1989), which is incorporated by reference herein in its entirety.

The present invention provides for transgenic animals that carry the CDC14A transgene in all their cells, as well as animals which carry the transgene in some, but not all of their cells, i.e., mosaic animals. The transgene may be integrated as a single transgene or in concatamers, e.c., head-to-head tandems or head-to-tail tandems. The transgene may also be selectively introduced into and activated in a particular cell type by following, for example, the teaching of Lasko et al. (1992). The regulatory sequences required for such a cell-type specific activation will depend upon the particular cell type of interest, and will be apparent to those of skill in the art. When it is desired that the CDC14A gene transgene be integrated into the chromosomal site of the endogenous CDC14A gene, gene targeting is preferred. Briefly, when such a technique is to be utilized, vectors containing some nucleotide sequences homologous to the endogenous CDC14A gene are designed for the purpose of integrating, via homologous recombination with chromosomal sequences, into and disrupting the function of the nucleotide sequence of the endogenous CDC14A gene. The transgene may also be selectively introduced into a particular cell type, thus inactivating the endogenous CDC14A gene in only that cell type, by following, for example, the teaching of Gu et al. (1994). The regulatory sequences required for such a cell-type specific inactivation will depend upon the particular cell type of interest, and will be apparent to those of skill in the art.

Once transgenic animals have been generated, the expression of the recombinant CDC14A gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of CDC14A gene-expressing tissue, may also be evaluated immunocytochemically using antibodies specific for the CDC14A transgene product.

Antisense polynucleotide sequences are useful in preventing or diminishing the expression of the CDC14A locus, as will be appreciated by those skilled in the art. For example, polynucleotide vectors containing all or a portion of the CDC14A locus or other sequences from the CDC14A region (particularly those flanking the CDC14A locus) may be placed under the control of a promoter in an antisense orientation and introduced into a cell. Expression of such an antisense construct within a cell will interfere with CDC14A transcription and/or translation and/or replication.

The probes and primers based on the CDC14A gene sequences disclosed herein are used to identify homologous CDC14A gene sequences and proteins in other species. These CDC14A gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of an CDC14A allele predisposing an individual to cancer, a biological sample such as blood is prepared and analyzed for the presence or absence of susceptibility alleles of CDC14A. In order to detect the presence of neoplasia, the progression toward malignancy of a precursor lesion, or as a prognostic indicator, a biological sample of the lesion is prepared and analyzed for the presence or absence of mutant alleles of CDC14A. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant CDC14A sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding CDC14A. Allele specific probes are also contemplated within the scope of this example and exemplary allele specific probes include probes encompassing the predisposing or potentially predisposing mutations described herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting CDC14A. Thus, in one example to detect the presence of CDC14A in a cell sample, more than one probe complementary to CDC14A is employed and in particular the number of different probes is alternatively 2, 3, or 5 different nucleic acid probe sequences. In another example, to detect the presence of mutations in the CDC14A gene sequence in a patient, more than one probe complementary to CDC14A is employed where the cocktail includes probes capable of binding to the allele-specific mutations identified in populations of patients with alterations in CDC14A. In this embodiment, any number of probes can be used, and will preferably include probes corresponding to the major gene mutations identified as predisposing an individual to prostate cancer.

Methods of Use: Peptide Diagnosis and Diagnostic Kits

The neoplastic condition of lesions can also be detected on the basis of the alteration of wild-type CDC14A polypeptide. Such alterations can be determined by sequence analysis in accordance with conventional techniques. More preferably, antibodies (polyclonal or monoclonal) are used to detect differences in, or the absence of, CDC14A peptides. The antibodies may be prepared as discussed above under the heading "Antibodies" and as further shown in Examples 9 and 10. Other techniques for raising and purifying antibodies are well known in the art and any such techniques may be chosen to achieve the preparations claimed in this invention. In a preferred embodiment of the invention, antibodies will immunoprecipitate CDC14A proteins from solution as well as react with CDC14A protein on Western or immunoblots of polyacrylamide gels. In another preferred embodiment, antibodies will detect CDC14A proteins in paraffin or frozen tissue sections, using immunocytochemical techniques.

Preferred embodiments relating to methods for detecting CDC14A or its mutations include enzyme linked immunosorbent assays (ELISA), radioimmunoassays (RIA), immunoradiometric assays (IRMA) and immunoenzymatic assays (IEMA), including sandwich assays using monoclonal and/ or polyclonal antibodies. Exemplary sandwich assays are described by David et al. in U.S. Pat. Nos. 4,376,110 and 4,486,530, hereby incorporated by reference, and exemplified in Example 12.

Methods of Use: Drug Screening

This invention is particularly useful for screening compounds by using the CDC14A polypeptide or binding fragment thereof in any of a variety of drug screening techniques.

The CDC14A polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an CDC14A polypeptide or fragment and the agent being tested, or examine the degree to which the formation of a complex between an CDC14A polypeptide or fragment and a known ligand is interfered with by the agent being tested.

Thus, the present invention provides methods of screening for drugs comprising contacting such an agent with an CDC14A polypeptide or fragment thereof and assaying (i) for the presence of a complex between the agent and the CDC14A polypeptide or fragment, or (ii) for the presence of a complex between the CDC14A polypeptide or fragment and a ligand, by methods well known in the art. In such competitive binding assays the CDC14A polypeptide or fragment is typically labeled. Free CDC14A polypeptide or fragment is separated from that present in a protein:protein complex, and the amount of free (i.e., uncomplexed) label is a measure of the binding of the agent being tested to CDC14A or its interference with CDC14A:ligand binding, respectively. One may also measure the amount of bound, rather than free, CDC14A. It is also possible to label the ligand rather than the CDC14A and to measure the amount of ligand binding to CDC14A in the presence and in the absence of the drug being tested.

Another technique for drug screening provides high throughput screening for compounds having suitable binding affinity to the CDC14A polypeptides and is described in detail in Geysen (published PCT WO 84/03564). Briefly stated, large numbers of different small peptide test compounds are synthesized on a solid substrate, such as plastic pins or some other surface. The peptide test compounds are reacted with CDC14A polypeptide and washed. Bound CDC14A polypeptide is then detected by methods well known in the art.

Purified CDC14A can be coated directly onto plates for use in the aforementioned drug screening techniques. However, non-neutralizing antibodies to the polypeptide can be used to capture antibodies to immobilize the CDC14A polypeptide on the solid phase.

This invention also contemplates the use of competitive drug screening assays in which neutralizing antibodies capable of specifically binding the CDC14A polypeptide compete with a test compound for binding to the CDC14A polypeptide or fragments thereof. In this manner, the antibodies can be used to detect the presence of any peptide which shares one or more antigenic determinants of the CDC14A polypeptide.

A further technique for drug screening involves the use of host eukaryotic cell lines or cells (such as described above) which have a nonfunctional CDC14A gene. These host cell lines or cells are defective at the CDC14A polypeptide level. The host cell lines or cells are grown in the presence of drug compound. The rate of growth of the host cells is measured to determine if the compound is capable of regulating the growth of CDC14A defective cells.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a two-hybrid system. This system may be used as a coarse screen prior to testing a substance for actual ability to modulate activity of the polypeptide. Alternatively, the screen could be used to screen test substances for binding to an CDC14A specific binding partner, or to find mimetics of an CDC14A polypeptide.

Methods of Use: Protein Interactions

The principles and methods of the yeast two-hybrid system have been described in detail elsewhere (e.g., Bartel and Fields, 1997; Bartel et al., 1993; Fields and Song, 1989; Chevray and Nathans, 1992; Lee et al., 1995). The following is a description of the use of this system to identify proteins that interact with a protein of interest, such as CDC14A.

The target protein is expressed in yeast as a fusion to the DNA-binding domain of the yeast Gal4p. DNA encoding the target protein or a fragment of this protein is amplified from cDNA by PCR or prepared from an available clone. The resulting DNA fragment is cloned by ligation or recombination into a DNA-binding domain vector (e.g., pGBT9, pGBT.C, pAS2-1) such that an in-frame fusion between the Gal4p and target protein sequences is created.

The target gene construct is introduced, by transformation, into a haploid yeast strain. A library of activation domain fusions (i.e., adult brain cDNA cloned into an activation domain vector) is introduced, by transformation into a haploid yeast strain of the opposite mating type. The yeast strain that carries the activation domain constructs contains one or more Gal4p-responsive reporter gene(s), whose expression can be monitored. Examples of some yeast reporter strains include Y190, PJ69, and CBY14a. An aliquot of yeast carrying the target gene construct is combined with an aliquot of yeast carrying the activation domain library. The two yeast strains mate to form diploid yeast and are plated on media that selects for expression of one or more Gal4p-responsive reporter genes. Colonies that arise after incubation are selected for further characterization.

The activation domain plasmid is isolated from each colony obtained in the two-hybrid search. The sequence of the insert in this construct is obtained by the dideoxy nucleotide chain termination method. Sequence information is used to identify the gene/protein encoded by the activation domain insert via analysis of the public nucleotide and protein databases. Interaction of the activation domain fusion with the target protein is confirmed by testing for the specificity of the interaction. The activation domain construct is co-transformed into a yeast reporter strain with either the original target protein construct or a variety of other DNA-binding domain constructs. Expression of the reporter genes in the presence of the target protein but not with other test proteins indicates that the interaction is genuine.

In addition to the yeast two-hybrid system, other genetic methodologies are available for the discovery or detection of protein-protein interactions. For example, a mammalian two-hybrid system is available commercially (Clontech, Inc.) that operates on the same principle as the yeast two-hybrid system. Instead of transforming a yeast reporter strain, plasmids encoding DNA-binding and activation domain fusions are transfected along with an appropriate reporter gene (e.g., lacZ) into a mammalian tissue culture cell line. Because transcription factors such as the *Saccharomyces cerevisiae* Gal4p are functional in a variety of different eukaryotic cell types, it would be expected that a two-hybrid assay could be performed in virtually any cell line of eukaryotic origin (e.g., insect cells (SF9), fungal cells, worm cells, etc.). Other genetic systems for the detection of protein-protein interactions include the so-called SOS recruitment system (Aronheim et al., 1997).

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., CDC14A polypeptide) or, for example, of the CDC14Areceptor or ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., CDC14A polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved CDC14A polypeptide activity or stability or which act as inhibitors, agonists, antagonists, etc. of CDC14A polypeptide activity. By virtue of the availability of cloned CDC14A sequences, sufficient amounts of the CDC14A polypeptide may be made available to perform such analytical studies as x-ray crystallography. In addition, the knowledge of the CDC14A protein sequence provided herein will guide those employing computer modeling techniques in place of, or in addition to x-ray crystallography.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment of prostate cancer, use of such a substance in the manufacture of a composition for administration, e.g., for treatment of prostate cancer, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Gene Therapy

According to the present invention, a method is also provided of supplying wild-type CDC14A function to a cell which carries mutant CDC14A alleles. Supplying such a function should suppress neoplastic growth of the recipient cells. The wild-type CDC14A gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant CDC14A allele, the gene fragment should encode a part of the CDC14A protein which is required for non-neoplastic growth of the cell. More preferred is the situation where the wild-type CDC14A gene or a part thereof is introduced into the mutant cell in such a way that it recombines with the endogenous mutant CDC14A gene present in the cell. Such recombination requires a double recombination event which results in the correction of the CDC14A gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of the practitioner. Cells transformed with the wild-type CDC14A gene can be used as model systems to study cancer remission and drug treatments which promote such remission.

As generally discussed above, the CDC14A gene or fragment, where applicable, may be employed in gene therapy methods in order to increase the amount of the expression products of such genes in cancer cells. Such gene therapy is particularly appropriate for use in both cancerous and pre-cancerous cells, in which the level of CDC14A polypeptide is absent or diminished compared to normal cells. It may also be useful to increase the level of expression of a given CDC14A gene even in those tumor cells in which the mutant gene is expressed at a "normal" level, but the gene product is not fully functional.

Gene therapy would be carried out according to generally accepted methods, for example, as described by Friedman (1991) or Culver (1996). Cells from a patient's tumor would be first analyzed by the diagnostic methods described above, to ascertain the production of CDC14A polypeptide in the tumor cells. A virus or plasmid vector (see further details below), containing a copy of the CDC14A gene linked to expression control elements and capable of replicating inside the tumor cells, is prepared. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient, either locally at the site of the tumor or systemically (in order to reach any tumor cells that may have metastasized to other sites). If the transfected gene is not permanently incorporated into the genome of each of the targeted tumor cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses, e.g., SV40 (Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpes viruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al, 1989; Stewart et al., 1992;

Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1991; Curiel et al., 1992). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes CDC14A, expression will produce CDC14A. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to prostate tissues, e.g., epithelial cells of the prostate, are preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. One appropriate receptor/ligand pair may include the estrogen receptor and its ligand, estrogen (and estrogen analogues). These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy involves two steps which can be performed singly or jointly. In the first step, prepubescent females who carry an CDC14A susceptibility allele are treated with a gene delivery vehicle such that some or all of their mammary ductal epithelial precursor cells receive at least one additional copy of a functional normal CDC14A allele. In this step, the treated individuals have reduced risk of prostate cancer to the extent that the effect of the susceptible allele has been countered by the presence of the normal allele. In the second step of a preventive therapy, predisposed young females, in particular women who have received the proposed gene therapeutic treatment, undergo hormonal therapy to mimic the effects on the prostate of a full term pregnancy.

Methods of Use: Peptide Therapy

Peptides which have CDC14A activity can be supplied to cells which carry mutant or missing CDC14A alleles. Protein can be produced by expression of the cDNA sequence in bacteria, for example, using known expression vectors. Alternatively, CDC14A polypeptide can be extracted from CDC14A-producing mammalian cells. In addition, the techniques of synthetic chemistry can be employed to synthesize CDC14A protein. Any of such techniques can provide the preparation of the present invention which comprises the CDC14A protein. Preparation is substantially free of other human proteins. This is most readily accomplished by synthesis in a microorganism or in vitro.

Active CDC14A molecules can be introduced into cells by microinjection or by use of liposomes, for example. Alternatively, some active molecules may be taken up by cells, actively or by diffusion. Extracellular application of the CDC14A gene product may be sufficient to affect tumor growth. Supply of molecules with CDC14A activity should lead to partial reversal of the neoplastic state. Other molecules with CDC14A activity (for example, peptides, drugs or organic compounds) may also be used to effect such a reversal. Modified polypeptides having substantially similar function are also used for peptide therapy.

Methods of Use: Transformed Hosts and Transgenic/Knockout Animals

Similarly, cells and animals which carry a mutant CDC14A allele can be used as model systems to study and test for substances which have potential as therapeutic agents. Cells may be isolated from individuals with CDC14A mutations, either somatic or germline. Alternatively, the cell line can be engineered to carry a mutation in the CDC14A allele, or the CDC14A allele can be deleted. After a test substance is applied to the cells, the neoplastically transformed phenotype of the cell is determined. Any trait of neoplastically transformed cells can be assessed, including anchorage-independent growth, tumorigenicity in nude mice, invasiveness of cells, and growth factor dependence. Assays for each of these traits are known in the art.

Animals for testing therapeutic agents can be selected after mutagenesis of whole animals or after treatment of germline cells or zygotes. Such treatments include insertion of mutant CDC14A alleles, usually from a second animal species, as well as insertion of disrupted homologous genes. Alternatively, the endogenous CDC14A gene(s) of the animals may be disrupted by insertion or deletion mutation or other genetic alterations using conventional techniques (Capecchi, 1989; Valancius and Smithies, 1991; Hasty et at., 1991; Shinkai et al., 1992; Mombaerts et al., 1992; Philpott et al., 1992; Snouwaert et al., 1992; Donehower et al., 1992) to produce knockout or trans placement animals. A transplacement is similar to a knockout because the endogenous gene is replaced, but in the case of a transplacement the replacement is by another version of the same gene. After test substances have been administered to the animals, the growth of tumors must be assessed. If the test substance prevents or suppresses the growth of tumors, then the test substance is a candidate therapeutic agent for the treatment of the cancers identified herein. These animal models provide an extremely important testing vehicle for potential therapeutic products.

The DNA encoding the protein of interest can be used to create animals that overexpress said protein, with wild-type or mutant sequences (such animals are referred to as "transgenic"), or animals which do not express the native gene but express the gene of a second animal (referred to as "transplacement"), or animals that do not express said protein (referred to as "knock-out"). The knock-out animal may be an animal in which the gene is knocked out at a determined time. The generation of transgenic, transplacement and knock-out animals (normal and conditioned) uses methods well known to those skilled in the art.

In one embodiment of the invention, transgenic animals are produced which contain a functional transgene encoding a functional CDC14A polypeptide or variants thereof. Transgenic animals expressing CDC14A transgenes, recombinant cell lines derived from such animals and transgenic embryos may be useful in methods for screening for and identifying agents that induce or repress function of CDC14A. Transgenic animals of the present invention also can be used as models for studying indications such as cancers.

A CDC14A transgene is introduced into a non-human host to produce a transgenic animal expressing a human or murine CDC14A gene. The transgenic animal is produced by the integration of the transgene into the genome in a manner that permits the expression of the transgene. Methods for producing transgenic animals are generally described by Brinster et al. (1985), Hogan et al. (1994), U.S. Pat. No. 4,873,191 and in "Manipulating the Mouse Embryo; A Laboratory Manual" 2nd edition (eds., Hogan et al., Cold Spring Harbor Laboratory Press, 1994), each of which is incorporated herein by reference in its entirety). Alternatively, the endogenous CDC14A gene(s) of the animals may be disrupted by insertion or deletion mutation or other genetic alterations using conventional techniques (as described above) to produce knockout or transplacement animals. A transplacement is similar to a knockout because the endogenous gene is replaced, but in the case of a transplacement the replacement is by another version of the same gene.

It may be desirable to replace the endogenous CDC14A by homologous recombination between the transgene and the endogenous gene; or the endogenous gene may be eliminated by deletion as in the preparation of "knock-out" animals. Typically, a CDC14A gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress CDC14A or express a mutant form of the polypeptide. Alternatively, the absence of a CDC14A in "knock-out" mice permits the study of the effects that loss of CDC14A protein has on a cell in vivo. Knock-out mice also provide a model for the development of CDC14A-related cancers.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant CDC14A may be exposed to test substances. These test substances can be screened for the ability to reduce overepression of wild-type CDC14A or impair the expression or function of mutant CDC14A.

Pharmaceutical Compositions and Routes of Administration

The CDC14A polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

The identification of the association between CDC14A gene mutations and certain cancers permits the early presymptomatic screening of individuals to identify those at risk for developing such cancer. To identify such individuals, CDC14A alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal CDC14A gene or appropriate fragment (coding sequence or genomic sequence) are determined and then compared, or (2) the RNA transcripts of the CDC14A gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the CDC14A gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal CDC14A gene.

Alternatively, polymerase chain reactions (PCRs) are performed with primer pairs for the 5 region or the exons of the CDC14A gene. PCRs can also be performed with primer pairs based on any sequence of the normal CDC14A gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common CDC14A gene variants by amplifying the individual s DNA using suitable primer pairs and analyzing the amplified product, e.g., by dot-blot hybridization using allele-specific oligonucleotide probes.

The second method employs RNase A to assist in the detection of differences between the normal CDC14A gene and defective genes. This comparison is performed in steps using small (~500 bp) restriction fragments of the CDC14A gene as the probe. First, the CDC14A gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the CDC14A gene fragments are transcribed in vitro using the SP6 transcription system, well known in the art, in the presence of [$\alpha$-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the CDC14A fragment and the CDC14A allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the CDC14A. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk prostate cancer, at, or even before, birth. Presymptomatic diagnosis of these epilepsies will enable prevention of these disorders.

EXAMPLES

The present invention is further detailed in the following Examples, which are offered by way of illustration and are not intended to limit the invention in any manner. Standard techniques well known in the art or the techniques specifically described below are utilized.

Example 1

Mutation Screening

Human tumor cell lines of various cancer types were obtained from ATCC. Total RNAs and genomic DNA were prepared in the same step using the TRI Reagent (Molecular Research Center). RNAs were reversed transcribed with Superscript II (GIBCO/BRL) to generate first strand cDNAs. Using these cDNA templates and the primers listed in Table 1, nested PCR amplifications and dye-primer sequencing reactions were performed to screen the entire open reading frame of CDC14 for alterations according to the protocol described previously by Teng et al (1997). Briefly, 1 ng of first-strand cDNA was used in each 20 µl primary PCR. Two sets of primary amplicons encompassing the entire gene were generated with the following CDC14 primary primer pairs: 1A-1P and 2A-2P. Each primary product was diluted 50-fold for a secondary amplification with the corresponding nested primer pairs: B-Q, C-R, D-S and E-T which have M13 sequence primer tails. The amplified products of the secondary reactions were subsequently subjected to Sanger dideoxy-terminator sequencing with dye-labeled M13 forward and reverse primers (Sanger et al, 1977). Greater than 95% coverage of the CDC14 coding sequence was obtained for every tumor cell line screened. All detected sequence variants were confirmed by sequencing a newly amplified product.

TABLE 1

Primers for Amplification of the Coding Region of CDC14A

| Name | Sequence (SEQ ID NO:) |
|---|---|
| cdc14.1A | CTCCCTCGGCCAGGCTTGTTG (3) |
| cdc14.1P | TTGAAAGATTTCCACCAATAGACAT (4) |
| cdc14.1B | GTTTTCCCAGTCACGACGTGACCTCAGCTGGCCACGAC (5) |
| cdc14.1Q | AGGAAACAGCTATGACCATTTCCGTTGGTCAAAACAGGTG (6) |
| cdc14.1C | GTTTTCCCAGTCACGACGGATATTGCTGCAAACTAAACAAG (7) |
| cdc14.1R | AGGAAACAGCTATGACCATCCACATCAATTGTCTCAAAGTCA (8) |
| cdc14.1D | GTTTTCCCAGTCACGACGATCTCACCATTCTCGACTGTTTG (9) |
| cdc14.1S | AGGAAACAGCTATGACCATTGCTCGAAGCCAGCGTCTGTG (10) |
| cdc14.1E | GTTTTCCCAGTCACGACGTATTTCAAAAAGCATAATGTGACT (11) |
| cdc14.1T | AGGAAACAGCTATGACCATGGGGTCCTATAATAGAGCCTG (12) |
| cdc14.2A | CATCTGTGAGAACACCGAAGGG (13) |
| cdc14.2P | GCATTTATAGTAGTCATTAACCAG (14) |
| cdc14.2B | GTTTTCCCAGTCACGACGTATGTAATGAAACACTACAGGTT (15) |
| cdc14.2Q | AGGAAACAGCTATGACCATTTTTCATTTCCACATCATCATCT (16) |
| cdc14.2C | GTTTTCCCAGTCACGACGATATGTCTATTGGTGGAAATCTT (17) |
| cdc14.2R | AGGAAACAGCTATGACCATTTGCTGAAGGGGACAGTGCCA |

TABLE 1-continued

Primers for Amplification of the Coding Region of CDC14A

| Name | Sequence (SEQ ID NO:) |
|---|---|
|  | (18) |
| cdc14.2D | GTTTTCCCAGTCACGACGGCCTTTCAGATTAAGTTCATCC (19) |
| cdc14.2S | AGGAAACAGCTATGACCATGCTCAGGGTAATTTCTGGTAGT (20) |
| cdc14.2E | GTTTTCCCAGTCACGACGCTTCACAGCCAGCCCGTTTAC (21) |
| cdc14.2T | AGGAAACAGCTATGACCATCTCTCCACTGCTCGTCCAGAT (22) |

Analysis of tumor cell line genomic DNAs for homozygous deletions of CDC14 were performed by PCR with the following two primer pairs: cdc14.F1/R1 and cdc14.F4/R4 which recognize the 5' and 3' end of the gene respectively (Table 2, set 1). Presence of a PCR product with the expected size indicates that the region was not deleted in the genome.

TABLE 2

Primers for amplification in the genomic region of CDC14A

| Primer | Sequence (SEQ ID NO:) | Sequence Length |
|---|---|---|
| (Set One) |  |  |
| cdc14.F1 | CGCTGACCCCGAAGCCGCCT (23) | 193 bp |
| cdc14.R1 | CGATTAGTTCCCTGACTCCGC (24) |  |
| cdc14.F4 | TTTGGGAAGTCAGTTTAGTTACAC (25) | 199 bp |
| cdc14.R4 | CAGAAGAAATATTCAGTGAATTCT (26) |  |
| cdc14.F10 | TAAGTTCATCCCTGCAAGGATCT (27) | 98 bp |
| cdc14.R10 | ACAAAGAAGTTCTGTTGATCCTC (28) |  |
| (Set Two) |  |  |
| 113i9.SP6F | GCCAGACAAGAGGCACAGATTC (29) | 224 bp |
| 113i9.SP6R | AGTCACCTTTCAAATACTGCGG (30) |  |
| 113i9.T7F | GAGGAGACCTGGGTGGCTAGA (31) | 222 bp |
| 113i9.T7R | GTGCAAGCACCATTATTCCCTC (32) |  |
| 156g7.T7F | GACAGAGGGCAGATCCATGAAG (33) | 172 bp |
| 156g7.T7R | CCAGGCACTGAAATAACTCACC (34) |  |
| 5a18.SP6F | GGGATAAGACATCGAATGTTCACA (35) | 139 bp |
| 5a18.SP6R | TAACATCCAGGGATCTAGTTCTGA (36) |  |
| 64a23.SP6F | TTAAAGCTACAGAGCATTCATTCA (37) | 174 bp |
| 64a23.SP6R | TTTCACTCAGAATTTGCATAATCC (38) |  |
| 64a23.T7F | TGAGTTTCTATGAGGGAGCCAG (39) | 161 bp |
| 64a23.T7R | TGCCAGGCACTCTTCTAGGCAT (40) |  |

TABLE 2-continued

Primers for amplification in the genomic region of CDC14A

| Primer | Sequence (SEQ ID NO:) | Sequence Length |
|---|---|---|
| 82h2.SP6F | AGAGTCGAGAAAGGAAGAGCCA (41) | 146 bp |
| 82h2.SP6R | TAAGCCTGAACCCTAGCACTTG (42) | |
| 77a8.SP6F | TATACAGAATCACCTTGACAAACT (43) | 164 bp |
| 77a8.SP6R | GTACATAATATGTGCTGAGTGCT (44) | |
| 77a8.T7F | ATAATTACTTGAGAGATATTGGATA (45) | 123 bp |
| 77a8.T7R | ATTAAACCTCAAGCATAGCTTCTA (46) | |
| (Set Three) | | |
| 14del.F1 | CCATTTGCAAGGTTTCTCCC (47) | 354 bp |
| 14del.R1 | AATCCTTTTCATGGTGAGCATT (48) | |
| 14del.F2 | TTGATACCATTTGATGTGCCT (49) | 220 bp |
| 14del.R2 | GTTGATTTTCGTGTTTGAGGC (50) | |

We investigated if CDC14A was aberrant in 138 tumor cell lines derived from different tissue types including brain, breast, colon, ovary, lung, pancreas, stomach, endometrium, prostate, skin, bladder, testis and skin. Each cell line was screened for homozygous deletions and coding sequence alteration in the CDC14 A gene. Using STSs specific for the 5' and 3' untranslated region of the CDC14 A gene, PCR was performed to test for amplification from genomic DNA. Reproducible absence of PCR products would indicate homozygous deletions. We detected PCR products of the correct size in all the cell lines examined indicating that at least the 5' and 3' end of the gene were not deleted. However this screen alone did not rule out the possibility that there could be microdeletions and other sequence variations in the coding region of the gene.

In the screening the CDC14A open reading frame (ORF) by sequence analysis, we developed eight overlapping amplicons of approximately 300–350 bp each that spanned the coding portion of its cDNA. These fragments were subjected to dye-primer or dye-terminator fluorescent sequencing in both directions. We found three discrepancies between the consensus CDC14A sequence established from our screen and that previously reported by Li et al (1997, GenBank accession number AF000367). One sequence difference occurred at nucleotide position 448 of the Li et al.'s ORF (490 of SEQ ID NO:1), which was a T and not an A, with a predicted amino acid change from isoleucine to phenylalanine. The second difference occurred at position 504 (546 of SEQ ID NO:1), which was a G and not a T, with an amino acid change from cysteine to tryptophan. The third discrepancy occurred at −24 position in the 5' untranslated region where there should be an additional G. This latter change introduces an alternative translational start site 14 amino acid residues upstream of the sequence reported by Li et al. (1997). The predicted amino acid sequence of the new reading frame is shown in Table 3 (SEQ ID NO:2). The differences between the sequence of the present invention and Li et al. are shown in bold.

TABLE 3

Sequence of CDC14A (SEQ ID NO:2)

MAAESGELIGACEFMKDRLYFATLRNRPKSTVNTHYFSIDEELVYENFYA
DFGPLNLAMVYRYCCKLNKKLKSYSLSRKKIVHYTCFDQRKRANAAFLIG
AYAVIYLKKTPEEAYRALLSGSNPPYLPFRDASFGNCTYNLTILDCLQGI
RKGLQHGFFDFETFDVDEYEHYERVENGDFNWIVPGKFLAFSGPHPKSKI
ENGYPLHAPEAYFPYFKKHNVTAVVRLNKKIYEAKRFTDAGFEHYDLFFI
DGSTPSDNIVRRFLNICENTEGAIAVHCKAGLGRTGTLIACYVMKHYRFT
HAEIIAWIRICRPGSIIGPQQHFLEEKQASLWVQGDIFRSKLKNRPSSEG
SINKILSGLDDMSIGGNLSKTQNMERFGEDNLEDDDVEMKNGITQGDKLR
ALKSQRQPRTSPSCAFRSDDTKGHPRAVSQPFRLSSSLQGSAVTLKTSKM
ALSPSATAKRINRTSLSSGATVRSFSINSRLASSLGNLNAATDDPENKKT
SSSSKAGFTASPFTNLLNGSSQPTTRNYPELNNNQYNRSSNSNGGNLNSP
PGPHSAKTEEHTTILRPSYTGLSSSSARFLSRSIPSLQSEYVHY

In the course of preparing samples for sequence analysis, we observed that the PCR product of amplicon 2CR in the breast cell line, MDA-MB-436, migrated faster on an agarose gel. This smaller size band indicated a small deletion in this cDNA sample. Interestingly we did not observe it in the other 23 breast cell lines or any other tumor cell lines that were examined. Upon sequencing of the cDNA from MDA-MB-436, it was shown that the 48 bp from nucleotide position 1251–1298 of SEQ ID NO:2 which is in frame with the coding region were deleted. Also the expression of the wild type allele in this cell line was not detected in our PCR assay. This observation was interpretated as apparent loss of heterozygosity across the CDC14A locus in this breast cancer cell line.

Screening of the CDC14A coding sequences of the remaining tumor cell lines revealed the T903C, G990A, C1647T variants in a number of cell lines that are predicted to be silent (Table 4). These silent changes likely represent polymorphisms. We had also found two heterozygotes with nonconserved missense changes. One in brain cell line D283Med and the other in HCT15 that resulted in a glycine to arginine and leucine to proline change respectively.

TABLE 4

Summary of CDC14A Sequence Variants from cDNA Mutation Screening

| Cell line | Tissue | Alteration | Genotype | Predicted Effect |
|---|---|---|---|---|
| SCaBER+ | Bladder | T903C | Het | Silent |
| LS180# | colon | G990A | Het | Silent |
| OV-1063* | ovarian | G990A | H | Silent |
| MDA-MB-436 | breast | delete 1251–1298 | H | In frame deletion |
| MDA-MB-157 | breast | C1647T | H | Silent |
| D283 Med | brain | G1711A | Het | Gly to Arg |
| HCT15 | colon | T1715C | Het | Leu to Pro |

H, hemizygosity, homozygosity or loss of expression.
Het, heterozygosity.
Total of 14 (#), 4 (*) and 2 (+) cell lines have similar variations.

Example 2

BAC Preparation and Radiation Hybrid Map

Initial screening of the BAC library from Genome System was performed with the following primer pairs: cdc14.F1/

R1, cdc14.F2/R2 and cdc14.F10/R10 (Table 2, set 1). Six clones, 113i9, 156g7, 5a18, 64a23, 82h2 and 77a8 were obtained for DNA preparation using the NucleoBond Kit from Clontech. The ends of each BAC were sequenced directly with the standard sequencing primers T7 and SP6. Based on the sequence information, new sequence tag site (STS) primers (Table 2, set 2) were designed to detect if the BACs overlap and to place them into a contig. Size of each BAC after digestion with NotI or SalI was determined by pulse field gel electrophoresis using the CHEF-DRIII module.

For mapping of the chromosome location, the primer pair 64a23.T7F/R (Table 2, set 2) designed to recognize the human chromosomal region of CDC14, but not to hamster DNA was used to screen a human-hamster hybrid cell line panel (Genebridge panel 4 from Human Genome Project, Sanger Center).

The chromosomal location of CDC14A was determined by performing radiation hybrid mapping. Using the GeneBridge 4 human/hamster somatic cell hybrid mapping panel, we performed a series of PCR reactions with two STSs from the CDC14A genomic region. We found that this gene is localized at 2.22 cR telomeric to the Whitehead marker WI-3294. In the framework of the Whitehead genetic map, this is approximately 312.67 cR from the top of chromosome 1 linkage group. Relative to a cytogenetic map, this gene is within the short arm region of chromosome 1 at or near 1p21. If CDC14A plays the role of a tumor suppressor, loss of heterozygosity in this gene region might be apparent in certain tumors. Indeed two studies have shown that losses of 1p21–22 are found in highly differentiated breast carcinoma (Schwendel et al, 1998) and allelic losses of 1p22–p31 are correlated with lymph node metastasis (Tsukamoto et al, 1998) and 1p22 with malignant mesothelioma (Lee et al, 1996). It will be of interest to determine if CDC14A plays a causal role in these tumor types.

Example 3

Mapping of Intron/Exon Structure

Primers based on the CDC14 cDNA sequence were designed at 100 bp intervals and used to sequence the BACs directly to map the intron/exon junctions. Specifically BAC 156g7, 64a23 and 77a8 were used to map exon 1–4, 5–10, 11–16 respectively. For the amplification of exon 13, primers pairs 14del.F1/R1 and 14del.F2/R2 (Table 2, set 3) complementary to the flanking intronic sequences were used in a single round PCR. The amplified products were treated with exonuclease and alkaline phosphatase to remove the original primer pool before sequencing with the same PCR primers and sequence primers specific to exon 13 d14SF1a: GTCAGATGATACAAAAGGACA (SEQ ID NO:51) and d14SR1a: TGAAAGGCTGGGACACTGCT (SEQ ID NO:52).

There were at least three possible explanations that might account for the 48-bp in-frame deletion in MDA-MB-436: (i) a small homozygous deletion in the genome eliminated this segment of the gene, (ii) a splice junction mutation altered processing of the mRNA, or (iii) it is a normal, but rare alternatively spliced mRNA form of CDC14A. To distinguish among these possibilities, we mapped the genomic structure of the CDC14A gene. A human BAC library was screened by PCR with CDC14A specific STSs. Six BACs were recovered to facilitate our mapping analysis. The insert of each BAC was sized by pulse field gel electrophoresis, and the ends of each BAC was sequenced with SP6 and T7 to generate new STSs which were used to map the order of the BACs. A physical contig map of the genomic region encompassing CDC14A locus was generated as shown in the Figure. BAC156g7, BAC64a23 and BAC77a8 were further chosen to identify the intron/exon junctions by direct sequencing. As shown in Table 5, 16 exons were identified in the gene. The 5' donor and 3' acceptor splice site junctions are as shown in bold for each exon. Upper and lower case letters correspond to exon and intron sequences, respectively. The nucleotide position of each exon corresponding to the coding region of the gene is based on SEQ ID NO:1. Exon 1 contains two possible start codon and the entire 5' UTR and exon 16 contains the 3' UTR with the stop codon. Exon 13 corresponding to nucleotide position 1251 to 1298 of the CDC14 open reading frame was the region deleted in the cDNA of cell line MDA-MB-436. We have also found that the two putative alternatively spliced variants of CDC14A deposited in GenBank (accession numbers AF064102 and AF064103) are likely to be artifacts. They both contained contiguous intronic sequences, thus suggesting that the clones sequenced were from unprocessed mRNA.

TABLE 5

Intron/Exon Junctions

| Acceptor Splice Site (SEQ ID NO:) | Donor Splice Site (SEQ ID NO) | Coding Sequence Position |
|---|---|---|
| ................................ | TTCATGAAAGgtgaggagca (53) | 1–49 |
| tgtctttcagATCGGTTATA (54) | TCTATGAAAAgtaagtttat (55) | 50–140 |
| tgtatcttagTTTCTATGCA (56) | GAAACTAAAAgtgagtattg (57) | 141–216 |
| ctctttctagTCATACAGTT (58) | TGCCTATGCAgtaagtacct (59) | 217–309 |
| tctgtcttagGTAATCTATT (60) | TTCCATTCAGgtataactcc (61) | 310–389 |
| atgtttatagGGATGCTTCC (62) | AATCAGAAAGgtaataacaa (63) | 390–456 |
| ctgcttttagGGATTACAAC (64) | ACATTATGAGgtttgtacat (65) | 457–519 |
| attctgccagCGAGTTGAAA (66) | ATTGAGAATGgtaggttttt (67) | 520–607 |
| gttcctttagGTTATCCTCT (68) | CACTGCAAAGgtgtgtgcaa (69) | 608–838 |
| tctcttacagCTGGTCTTGG (70) | TCCTGGAAGAgtaagtatat (71) | 839–977 |
| tattatacagAAAGCAAGCA (72) | ATTTGGAGAGgtaagtcttc (73) | 978–1137 |
| tttttccagGATAACTTAG (74) | GTGCATTTAGgtagatctgt (75) | 1138–1250 |
| gtgcatttagGTCAGATGAT (76) | AGCCTTTCAGgtactgccaa (77) | 1251–1298 |
| ctccgcaaagATTAAGTTCA (78) | CTGTAAGAAGgtaatttttc (79) | 1299–1421 |

TABLE 5-continued

Intron/Exon Junctions

| Acceptor Splice Site (SEQ ID NO:) | Donor Splice Site (SEQ ID NO) | Coding Sequence Position |
|---|---|---|
| ttccattcagCTTTTCCATA (80) | TTCTATCCCTgtaagtgcgc (81) | 1422–1755 |
| ccctgcacagTCCCTTCAGT (82) | | 1756–1785 |

To elucidate if exon 13 was deleted due to homozygous deletion or splice site mutation in MDA-MB-436, two independent sets of primers specific to the intronic sequences flanking the exon were used to amplify genomic DNA from normal breast tissue and MDA-MB-436. The amplification of PCR products with the correct size from MDA-MB-436 genomic DNA indicated that this region was not microdeleted. Next we examined the PCR products by sequencing. We found that the invariant AG at the acceptor splice site of exon 13 in the normal genomic DNA is changed to AT in the breast tumor cell line DNA. Furthermore, we did not detect the wild type splice site sequence AG, indicating hemizygosity or homozygosity across this genomic region in MDA-MB-436. This was consistent with the lack of wild type CDC14A expression in this cell line. This alteration accounts for the 48 bp deletion in the message transcribed from the mutant allele. Interestingly, there is an accompanying loss of expression of the wild type allele in same breast cell line, further supporting CDC14A as a tumor suppressor.

Example 4

Generation of Polyclonal Antibody Against CDC14A

Segments of CDC14A coding sequence are expressed as fusion protein in *E. coli*. The overexpressed proteins are purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of CDC14A coding sequence was cloned as a fusion protein in plasmid PET5A (Novagen, Inc., Madison, Wis.). After induction with IPTG, the overexpression of a fusion protein with the expected molecular weight is verified by SDS/PAGE. Fusion proteins are purified from the gel by electroelution. The identification of the protein as the CDC14A fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure can be repeated to generate antibodies against mutant forms of the CDC14A protein. These antibodies, in conjunction with antibodies to wild type CDC14A, are used to detect the presence and the relative level of the mutant forms in various tissues and biological fluids.

Example 5

Generation of Monoclonal Antibodies Specific for CDC14A

Monoclonal antibodies are generated according to the following protocol. Mice are immunized with immunogen comprising intact CDC14A or CDC14A peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly, P3.65.3 myeloma cells (American Type Culture Collection, Rockville, Md.) are fused with immune spleen cells using polyethylene glycol as described by Harlow and Lane (1988). Cells are plated at a density of $2 \times 10^5$ cells/well in 96 well tissue culture plates. Individual wells are examined for growth and the supernatants of wells with growth are tested for the presence of CDC14A specific antibodies by ELISA or RIA using wild type or mutant CDC14A target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 6

Identification of Proteins Interacting with CDC14A

The principles and methods of the yeast two-hybrid system have been described in detail elsewhere (e.g., Bartel and Fields, 1997). The following is a description of the use of this system to identify proteins that interact with CDC14A.

A sequence encoding all or portion of CDC14A is expressed in yeast as a fusion to the DNA-binding domain of the yeast Gal4p. DNA encoding the CDC14A protein or a fragment of this protein is amplified from cDNA by PCR or prepared from an available clone. The resulting DNA fragment is cloned by ligation or recombination into a DNA-binding domain vector (e.g., pGBT9, pGBT.C, pAS2-1) such that an in-frame fusion between the Gal4p and CDC14A protein sequences is created.

This CDC14A gene construct is introduced, by transformation, into a haploid yeast strain. A library of activation domain fusions (i.e., adult brain cDNA cloned into an activation domain vector) is introduced, by transformation into a haploid yeast strain of the opposite mating type. The yeast strain that carries the activation domain constructs contains one or more Gal4p-responsive reporter gene(s), whose expression can be monitored. Examples of some yeast reporter strains include Y190, PJ69, and CBY14a. An aliquot of yeast carrying the CDC14A gene construct is combined with an aliquot of yeast carrying the activation domain library. The two yeast strains mate to form diploid yeast and are plated on media that selects for expression of one or more Gal4p-responsive reporter genes. Colonies that arise after incubation are selected for further characterization of the protein interacting with CDC14A, including sequence analysis.

This procedure is repeated with mutant forms of the CDC14A gene, to identify proteins that interact with only the mutant protein or to determine whether a mutant form of the CDC14A protein can or cannot interact with a protein known to interact with wild-type CDC14A.

Example 7

Isolation of CDC14A Binding Peptides

Peptides that bind to the CDC14A gene product are isolated from both chemical and phage-displayed random peptide libraries as follows.

Fragments of the CDC14A gene product are expressed as GST and His-tag fusion proteins in both *E. coli* and SF9 cells. The fusion protein is isolated using either a glutathione matrix (for GST fusions proteins) or nickel chelation matrix (for His-tag fusion proteins). This target fusion protein preparation is either screened directly as described below, or eluted with glutathione or imidizole. The target protein is immobilized to either a surface such as polystyrene; or a resin such as agarose; or solid supports using either direct absorption, covalent linkage reagents such as glutaraldehyde, or linkage agents such as biotin-avidin.

Two types of random peptide libraries of varying lengths are generated: synthetic peptide libraries that may contain derivatized residues, for example by phosphorylation or myristylation, and phage-displayed peptide libraries which may be phosphorylated. These libraries are incubated with immobilized CDC14A gene product in a variety of physiological buffers. Next, unbound peptides are removed by repeated washes, and bound peptides recovered by a variety of elution reagents such as low or high pH, strong denaturants, glutathione, or imidizole. Recovered synthetic peptide mixtures are sent to commercial services for peptide micro-sequencing to identify enriched residues. Recovered phage are amplified, rescreened, plaque purified, and then sequenced to determined the identity of the displayed peptides.

Peptides identified from the above screens are synthesized in larger quantities as biotin conjugates by commercial services. These peptides are used in both solid and solution phase competition assays with CDC14A and its interacting partners identified in yeast 2-hybrid screens. Versions of these peptides that are fused to membrane-permeable motifs (Lin et al., 1995; Rojas et al., 1996) are chemically synthesized, added to cultured cells and the effects on growth, apoptosis, differentiation, cofactor response, and internal changes are assayed.

Example 8

Sandwich Assay for CDC14A

Monoclonal antibody is attached to a solid surface such as a plate, tube, bead, or particle. Preferably, the antibody is attached to the well surface of a 96-well ELISA plate. 100 ml sample (e.g., serum, urine, tissue cytosol) containing the CDC14A peptide/protein (wild-type or mutant) is added to the solid phase antibody. The sample is incubated for 2 hrs at room temperature. Next the sample fluid is decanted, and the solid phase is washed with buffer to remove unbound material. 100 ml of a second monoclonal antibody (to a different determinant on the CDC14A peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of CDC14A peptide/protein present in the sample, is quantitated. Separate assays are performed using monoclonal antibodies which are specific for the wild-type CDC14A as well as monoclonal antibodies specific for each of the mutations identified in CDC14A.

Example 9

In vitro Identification of Modulators for CDC14A Interactions

The present invention is useful in screening for agents that modulate the interaction of CDC14A and interacting proteins identified in accordance with Example 6. The knowledge that a CDC14A containing complex is formed is useful in designing such assays. Candidate agents are screened by mixing the proteins of the complex (a) in the presence of a candidate agent, and (b) in the absence of the candidate agent. The amount of complex formed is measured for each sample. An agent modulates the interaction of the proteins if the amount of complex formed in the presence of the agent is greater than (promoting the interaction), or less than (inhibiting the interaction) the amount of complex formed in the absence of the agent. The amount of complex is measured by a binding assay, which shows the formation of the complex, or by using antibodies immunoreactive to the complex.

Briefly, a binding assay is performed in which immobilized CDC14A is used to bind a labeled interacting protein. The labeled interacting protein is contacted with the immobilized CDC14A under aqueous conditions that permit specific binding of the two proteins to form an the protein complex in the absence of an added test agent. Particular aqueous conditions may be selected according to conventional methods. Any reaction condition can be used as long as specific binding of complex occurs in the control reaction. A parallel binding assay is performed in which the test agent is added to the reaction mixture. The amount of labeled binding partner bound to the immobilized CDC14A is determined for the reactions in the absence or presence of the test agent. If the amount of bound, labeled interacting protein in the presence of the test agent is different than the amount of bound labeled interacting protein in the absence of the test agent, the test agent is a modulator of the interaction of CDC14A.

Example 10

In vivo Identification of Modulators for CDC14A Interaction

In addition to the in vitro method described in Example 9, an in vivo assay can also be used to screen for agents which modulate the interaction of CDC14A and interacting proteins. Briefly, a yeast two-hybrid system is used in which the yeast cells express (1) a first fusion protein comprising CDC14A or a fragment thereof and a first transcriptional regulatory protein sequence, e.g., GAL4 activation domain, (2) a second fusion protein comprising an interacting protein or a fragment thereof and a second transcriptional regulatory protein sequence, e.g., GAL4 DNA-binding domain, and (3) a reporter gene, e.g., β-galactosidase, which is transcribed when an intermolecular complex comprising the first fusion protein and the second fusion protein is formed. Parallel reactions are performed in the absence of a test agent as the control and in the presence of the test agent. A functional complex is detected by detecting the amount of reporter gene expressed. If the amount of reporter gene expression in the presence of the test agent is different than the amount of reporter gene expression in the absence of the test agent, the test agent is a modulator of the interaction of CDC14A.

The precise biological function of human CDC14A is not well understood. However, recent studies have shown that yeast CDC4 is a dual-specificity serine/threonine-tyrosine phosphatase whose activity is required for cell cycle function (Taylor et al, 1997; Grandin et al, 1998). Additionally some genetic studies have suggested that it may be involved in initiating DNA replication (Hardy, 1996). Although human CDC14A is a dual-specificity phosphatase, there is yet any convincing evidence to show that it shares similar targets and function in common biochemical pathways as MMAC1/PTEN. Nevertheless, the perturbation of pathways in cell cycle and/or DNA replication could have detrimental effects, such as leading to uncontrolled cell growth and/or inaccurate replication of essential genes.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1997). *Nucl. Acids Res.* 25:3389–3402.
Anand R (1992). *Techniques for the Analysis of Complex Genomes,* (Academic Press).
Anderson W F, et al. (1980). *Proc. Natl. Acad. Sci. USA* 77:5399–5403.
Aronheim et al. (1997). *Mol. Cell. Biol.* 17:3094–3102.
Ausubel F M, et al. (1992). *Current Protocols in Molecular Biology,* (J. Wiley and Sons, NY).
Bandyopadhyay P K and Temin H M (1984). *Mol. Cell. Biol.* 4:749–754.
Bartel, P. L. and Fields, S. (1997). The Yeast Two-Hybrid System. New York: Oxford University Press.
Bartel P L, et al. (1993). "Using the 2-hybrid system to detect protein-protein interactions." In: *Cellular Interactions in Development: A Practical Approach,* Oxford University Press, pp. 153–179.
Beaucage S L and Caruthers M H (1981). *Tetra. Letts.* 22:1859–1862.
Berglund P, et al. (1993). *Biotechnology* 11:916–920.
Berkner K L (1992). *Curr. Top. Microbiol. Immunol.* 158:39–66.
Berkner K L, et al. (1988). *BioTechniques* 6:616–629.
Borman S (1996). *Chemical & Engineering News,* December 9 issue, pp. 42–43.
Breakefield X O and Geller A I (1987). *Mol. Neurobiol.* 1:337–371.
Brinster R L, et al. (1981). Cell 27:223–231.
Brown, M. A., and Solomon, E. (1997). *Trends in Genet.* 13:202–6.
Buchschacher G L and Panganiban A T (1992). *J Virol.* 66:2731–2739.
Capecchi M R (1989). *Science* 244:1288–1292.
Cariello N F (1988). *Am. J. Human Genetics* 42:726–734.
Chee M, et al. (1996). *Science* 274:610–614.
Chevray P M and Nathans D N (1992). *Proc. Natl. Acad. Sci. USA* 89:5789–5793.
Compton J (1991). *Nature* 350:91–92.
Conner B J, et al. (1983). *Proc. Natl. Acad. Sci. USA* 80:278–282.
Costantini F and Lacy E (1981). *Nature* 294:92–94.
Cotton M, et al. (1990). *Proc. Natl. Acad. Sci. USA* 87:4033–4037.
Cotton R G, et al. (1988). *Proc. Natl. Acad. Sci. USA* 85:4397–4401.
Culver K W, et al. (1992). *Science* 256:1550–1552.
Curiel D T, et al. (1991). *Proc. Natl. Acad. Sci. USA* 88:8850–8854.
Curiel D T, et al. (1992). *Hum. Gene Ther.* 3:147–154.
DeRisi J, et al. (1996). *Nature Genetics* 14:457–460.
Deutscher, M (1990). *Meth. Enzymology* 182:83–89 (Academic Press, San Diego, Calif.).
Donehower L A, et al. (1992). *Nature* 356:215–221.
Editorial (1996). *Nature Genetics* 14:367–370.
Elghanian R, et al. (1997). *Science* 277:1078–1081.
*Enhancers and Eurkaryotic Gene Expression,* Cold Spring Harbor Press, Cold Spring Harbor, N.Y. (1983).
Eppert, K. et al. (1996). *Cell* 86:543–52.
Erickson J, et al. (1990). *Science* 249:527–533.
Fahy E, et al. (1991). *PCR Methods Appl.* 1:25–33.
Felgner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In: *Therapy for Genetic Diseases,* T. Friedman, ed., Oxford University Press, pp. 105–121.
Galaktionov, K. et al. (1995). CDC25 phosphatases as potential human oncogenes. *Science* 269:1575–7.
Glover D (1985). *DNA Cloning,* I and II (Oxford Press).
Goding (1986). *Monoclonal Antibodies: Principles and Practice,* 2d ed. (Academic Press, NY).
Godowski P J, et al. (1988). *Science* 241:812–816.
Gordon J W, et al. (1980). *Proc. Natl. Acad. Sci. USA* 77:7380–7384.
Gordon J W (1989). *Intl. Rev. Cytol.* 115:171–229.
Gorziglia M and Kapikian A Z (1992). *J. Virol.* 66:4407–4412.
Graham F L and van der Eb A J (1973). *Virology* 52:456–467.
Grandin, N. et al. (1998). *Mol. Gen. Genet.* 258:104–116.
Grompe M (1993). *Nature Genetics* 5:111–117.
Grompe M, et al. (1989). *Proc. Natl. Acad. Sci. USA* 86:5855–5892.
Gu H, et al. (1994). *Science* 265:103–106.
Guilford, P. et al. (1998). *Nature* 392:402–5.
Guthrie G and Fink G R (1991). *Guide to Yeast Genetics and Molecular Biology* (Academic Press).
Hacia J G, et al. (1996). *Nature Genetics* 14:441–447.
Hahn, S. A. et al. (1996). *Science* 271:350–3.
Harlow E and Lane D (1988). *Antibodies: A Laboratory Manual* (Cold Spring Harbor Laboratory, Cold Spring Harbor, N.Y.).
Hardy, C. F. (1996). *Mol. Cell. Biol.* 16:1832–41.
Hasty P, et al. (1991). *Nature* 350:243–246.

Helin, K. et al. (1997). *Proc. Natl. Acad. Sci. USA* 94:6933–8.
Helseth E, et al. (1990). *J. Virol.* 64:2416–2420.
Hiraguri, S. et al. (1998). *Cancer Res.* 58:1972–7.
Hodgson J (1991). *Bio/Technology* 9:19–21.
Hogan et al. (1994). *Manipulating the Mouse Embryo; A Laboratory Manual,* 2nd edition, Cold Spring Harbor Laboratory Press.
Howe, J. R. et al. (1998). *Science* 280:1086–8.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al (1986). *Nucl. Acids Res.* 14:6115–6128.
Jakoby W B and Pastan I H (eds.) (1979). *Cell Culture. Methods in Enzymology,* Vol. 58 (Academic Press, Inc., Harcourt Brace Jovanovich (NY)).
Johnson P A, et al. (1992). *J Virol.* 66:2952–2965.
Johnson, et al. (1993). "Peptide Turn Mimetics" In: *Biotechnology and Pharmacy,* Pezzuto et al., eds., Chapman and Hall, NY.
Kamb, A. et al. (1994). *Science* 264:436–440.
Kaneda Y, et al. (1989). *J Biol. Chem.* 264:12126–12129.
Kanehisa M (1984). *Nucl. Acids Res.* 12:203–213.
Kinszler K W, et al. (1991). *Science* 251:1366–1370.
Kohler G and Milstein C (1975). *Nature* 256:495–497.
Kubo T, et al. (1988). *FEBS Lett.* 241:119–125.
Kyte J and Doolittle R F (1982). *J. Mol. Biol.* 157:105–132.
Landegren U, et al. (1988). *Science* 242:229–237.
Lasko M, et al. (1992). *Proc. Natl. Acad. Sci. USA* 89:6232–6236.
Lavitrano M, et al. (1989). *Cell* 57:717–723.
Lee J E, et al. (1995). *Science* 268:836–844.
Lee, W. C. et al. (1996). *Cancer Res.* 56:4297–4301.
Li, J. et al. (1997). *Science* 275:1943–7.
Li, L. et al. (1997). *J. Biol. Chem.* 272:29403–6.
Lim C S, et al. (1991). *Circulation* 83:2007–2011.
Lin Y Z, et al. (1995). *J. Biol. Chem.* 270:14255–14258.
Lipshutz R J, et al. (1995). *BioTechniques* 19:442–447.
Lo CW (1983). *Mol. Cell. Biol.* 3:1803–1814.
Lockhart D J, et al. (1996). *Nature Biotechnology* 14:1675–1680.
Madzak C, et al. (1992). *J. Gen. Virol.* 73:1533–1536.
Maehama, T., and Dixon, J. E. (1998). *J. Biol. Chem.* 273:13375–8.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Margolskee R F (1992). *Curr. Top. Microbiol. Immunol.* 158:67–95.
Martin R, et al. (1990). *Bio Techniques* 9:762–768.
Matteucci M D and Caruthers M H (1981). *J. Am. Chem. Soc.* 103:3185.
Matthews J A and Kricka L J (1988). *Anal. Biochem.* 169:1.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miki, Y. et al. (1997). *Jpn. J. Cancer Res.* 88:701–4.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869–877.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel (1992). *Hum. Gene Ther.* 3:399–410.
Nabel E G, et al. (1990). *Science* 249:1285–1288.
Naldini L, et al. (1996). *Science* 272:263–267.
Newton C R, et al. (1989). *Nucl. Acids Res.* 17:2503–2516.
Nguyen Q, et al. (1992). *BioTechniques* 13:116–123.
Novack D F, et al. (1986). *Proc. Natl. Acad. Sci. USA* 83:586–590.
Ohi S, et al. (1990). *Gene* 89:279–282.
Orita M, et al. (1989). *Proc. Nat. Acad. Sci. USA* 86:2776–2770.
Osada, M. et al. (1998). *Nat. Med.* 4:839–43.
Page K A, et al. (1990). *J. Virol.* 64:5270–5276.
Parsons, R. (1998). *Curr. Opin. Oncol.* 10:88–91.
Pellicer A, et al. (1980). *Science* 209:1414–1422.
Petropoulos C J, et al. (1992). *J. Virol.* 66:3391–3397.
Philpott K L, et al. (1992). *Science* 256:1448–1452.
Quantin B, et al. (1992). *Proc. Natl. Acad. Sci. USA* 89:2581–2584. *Remington's Pharmaceutical Sciences,* 18th Ed. (1990, Mack Publishing Co., Easton, Pa.).
Rigby P W J, et al. (1977). *J. Mol. Biol.* 113:237–251.
Rojas M, et al. (1996). *J. Biol. Chem.* 271:27456–27461.
Rosenfeld M A, et al. (1992). *Cell* 68:143–155.
Ruano G and Kidd K K (1989). *Nuc. Acids Res.* 17:8392.
Russell D and Hirata R (1998). *Nature Genetics* 18:323–328.
Sambrook, J. et al. (1989). *Molecular Cloning: A Laboratory Manual.* Cold Spring Harbor Laboratory: Cold Spring Harbor, N.Y.
Sanger, F. et al. (1977). *Proc. Natl. Acad. Sci. U.S.A.,* 74, 5463–5466.
Sato, M. et al. (1998). *Hum. Genet.* 103:96–101.
Scharf, S. J. (1986). *Science* 233:1076–1078.
Schneider, G. et al. (1998). *Nature Genetics* 18:180–183.
Schwendel, A. et al. (1998). *Br. J. Cancer.* 78:806–811.
Scopes, R. (1982). *Protein Purification: Principles and Practice,* (Springer-Verlag, NY).
Sheffield, V. C. et al. (1989). *Proc. Natl. Acad. Sci. USA* 86:232–236.
Sheffield, V. C. et al. (1991). *Am. J Hum. Genet.* 49:699–706.
Shenk, T. E. et al. (1975). *Proc. Natl. Acad. Sci. USA* 72:989–993.
Shimada, T. et al. (1991). *J. Clin. Invest.* 88:1043–1047.
Shinkai, Y. et al. (1992). *Cell* 68:855–867.
Shoemaker, D. D. et al. (1996). *Nature Genetics* 14:450–456.
Snouwaert, J. N. et al. (1992). *Science* 257:1083–1088.
Sorge, J. et al. (1984). *Mol. Cell. Biol.* 4:1730–1737.
Spargo, C. A. et al. (1996). *Mol. Cell. Probes* 10:247–256.
Steck, P. A. et al. (1997). *Nat. Genet.* 15:356–62.
Stewart, M. J. et al. (1992). *Hum. Gene Ther.* 3:267–275.
Stratford-Perricaudet, L. D. et al. (1990). *Hum. Gene Ther.* 1:241–256.
Su, G. H. et al. (1998). *Cancer Res.* 58:2339–2342.
Taylor, G. S. et al. (1997). *J. Biol. Chem.* 272:24054–63.
Teng, D. H.-F. et al. (1997). *Cancer Res.* 57:4177–82.
Thompson. S. et al. (1989). *Cell* 56:313–321.
Tsukamoto, K. et al. (1998). *Cancer* 82:317–322.
Valancius V and Smithies O (1991). *Mol. Cell Biol.* 11:1402–1408.
Van der Putten H, et al. (1985). *Proc. Natl. Acad. Sci. USA* 82:6148–6152.
Wagner E, et al. (1990). i *Proc. Natl. Acad. Sci. USA* 87:3410–3414.
Wagner E, et al. (1991). *Proc. Natl. Acad. Sci. USA* 88:4255–4259.

Walker G T, et al. (1992). *Nucl. Acids Res.* 20:1691–1696.
Wang C Y and Huang L (1989). *Biochemistry* 28:9508–9514.
Wang, S. S. et al. (1998). *Science* 282:284–287.
Wartell R M, et al. (1990). *Nucl. Acids Res.* 18:2699–2705.
Wells J A (1991). *Methods in Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.
Wilkinson G W and Akrigg A (1992). *Nucleic Acids Res.* 20:2233–2239.
Wolff J A, et al. (1990). *Science* 247:1465–1468.
Wolff J A, et al. (1991). *BioTechniques* 11:474–485.
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Xu J, et al. (1998). *Nat. Genet.* 20:175–179.
Zenke M, et al. (1990). *Proc. Natl. Acad. Sci. USA* 87:3655–3659.
List of Patents and Patent Applications
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,376,110
U.S. Pat. No. 4,486,530
U.S. Pat. No. 4,554,101
U.S. Pat. No. 4,683,195
U.S. Pat. No. 4,683,202
U.S. Pat. No. 4,816,567
U.S. Pat. No. 4,868,105
U.S. Pat. No. 4,873,191
U.S. Pat. No. 5,252,479
U.S. Pat. No. 5,270,184
U.S. Pat. No. 5,409,818
U.S. Pat. No. 5,436,146
U.S. Pat. No. 5,455,166
U.S. Pat. No. 5,550,050
U.S. Pat. No. 5,691,198
U.S. Pat. No. 5,735,500
U.S. Pat. No. 5,747,469
Hitzeman et al., EP 73,675A
EP 225,807A
EP 425,731A
EP. 332,435A
WO 84/03564
WO 90/07936
WO 92/19195
WO 93/07282
WO 94/25503
WO 95/01203
WO 95/05452
WO 96/02286
WO 96/02646
WO 96/11698
WO 96/40871
WO 96/40959
WO 97/12635

What is claimed is:

1. An isolated nucleic acid sequence encoding a CDC14A polypeptide, said polypeptide having the amino acid sequence set forth in Seq ID No: 2.

2. The isolated nucleic acid sequence of claim 1 encoding a mutated form of the CDC14A polypeptide having the amino acid sequence set forth in Seq ID No: 2, wherein the mutation is selected from the group consisting of:
   (a) deletion of bases 1251–1298;
   (b) G1711A; and
   (c) T1715C.

3. An expression vector, which comprises the isolated nucleic acid sequence of claim 1, wherein said nucleic acid sequence is operably linked to a promoter that directs expression of said nucleic acid sequence.

4. A vector which comprises the isolated nucleic acid sequence of claim 1.

5. A host cell transformed in vitro with the vector of claim 4.

6. A method of producing a CDC14A polypeptide having the amino acid sequence set forth in Seq ID No: 2 comprising: (a) culturing the host cells of claim 5 under conditions suitable for the production of said CDC14A polypeptide and (b) recovering said CDC14A polypeptide.

7. The method of claim 6, which further comprises labeling the recovered polypeptide.

8. An isolated nucleic acid sequence encoding a CDC14A polypeptide having the nucleotide sequence (a) set forth in Seq ID No: 1; (b) the complement of the nucleotide sequence set forth in Seq ID No 1; or (c) an RNA molecule corresponding to the nucleotide sequence set forth in Seq ID No 1.

9. A vector which comprises the isolated nucleic acid sequence of claim 8.

10. A vector which comprises the isolated nucleic acid sequence of claim 8 and a replicon operative in a host cell.

11. An expression vector, which comprises the isolated nucleic acid sequence of claim 8, wherein the said nucleic acid sequence is operably linked to a promoter that directs expression of said nucleic acid sequence.

12. A host cell transformed in vitro with the vector of claim 11.

13. A method of producing a CDC14A polypeptide which is encoded by the nucleotide sequence of Seq ID No 1 comprising: (a) culturing the host cell of claim 12 under conditions suitable for the production of said CDC14A polypeptide; and (b) recovering said CDC14A polypeptide.

14. The method of claim 13, which further comprises labeling the recovered polypeptide.

* * * * *